US007524925B2

United States Patent
Bruce et al.

(10) Patent No.: US 7,524,925 B2
(45) Date of Patent: Apr. 28, 2009

(54) PROTEIN INTERACTION REPORTER AGENTS AND METHODS FOR USING SAME

(75) Inventors: James E. Bruce, Colfax, WA (US); Xiaoting Tang, Pullman, WA (US); Gerhard Munske, Pullman, WA (US)

(73) Assignee: Washington State University, Pullman, WA (US)

( * ) Notice: Subject to any disclaimer, the term of this patent is extended or adjusted under 35 U.S.C. 154(b) by 0 days.

(21) Appl. No.: 11/282,403

(22) Filed: Nov. 18, 2005

(65) Prior Publication Data

US 2006/0115871 A1 Jun. 1, 2006

Related U.S. Application Data

(60) Provisional application No. 60/629,396, filed on Nov. 18, 2004.

(51) Int. Cl.
*C07K 2/00* (2006.01)
*C07K 1/13* (2006.01)
*C07C 229/38* (2006.01)

(52) U.S. Cl. ........................ 530/300; 562/441
(58) Field of Classification Search ........................ None
See application file for complete search history.

(56) References Cited

U.S. PATENT DOCUMENTS 5,124,478 A 6/1992 Breipohl et al.

OTHER PUBLICATIONS

Von Mering et al. "Comparative Assessment of Large-Scale Data Sets of Protein-Protein Interactions", May 23, 2002, Nature, vol. 417. pp. 399-403.*
Vasilescu et al. "Identification of Protein-Protein Interactions Using In Vivo Cross-Linking And Mass Spectrometry", 2004, Proteomics, vol. 4. pp. 3845-3854.*
Swaim et al., "Unexpected products from the reaction of the synthetic cross-linker 3,3'-dithiobis(sulfosuccinimidyl propionate), DTSSP with peptides." J. Am. Soc. Mass. Spectrom., 2004, 15, 736-49.*
Schilling et al., "MS2Assign, automated assignment and nomenclature of tandem mass spectra of chemically crosslinked peptides." J. Am. Soc. Mass. Spec., 2003, 14, 834-50.*
Back et al., "Chemical cross-linking and mass spectrometry for protein structural modeling." J. Mol. Biol., 2003, 331, 303-13.*
Sinz, "Chemical cross-linking and mass spectrometry for mapping three-dimensional structures of proteins and protein complexes." J. Mass. Spectrom. 2003, 38, 1225-37.*
Trester-Zedlitz et al., "A modular cross-linking approach for exploring protein interactions." JACS, 2003, 125, 2416-25.*
Itoh et al., "Mapping of contact sites in complex formation between light-activated rhodopsin and transducin by covalent crosslinking: use of a chemically preactivated reagent." PNAS, 2001, 98, 4883-7.*
Alley et al., "Building a replisome solution structure by elucidation of protein-protein interactions in the bacteriophage T4 DNA polymerase holoenzyme." J. Biol. Chem., 2001, 276, 39340-9.*
Bennett et al. "Chemical cross-linking with thiol-cleavable reagents combined with differential mass spectrometric peptide mapping—a novel approach to assess intermolecular protein contacts." Protein Science, 2000, 9, 1503-18.*
Back et al. "A structure for the yeast prohibitin complex: Structure prediction and evidence from chemical crosslinking and mass spectrometry." Protein Science, 2002, 11, 2471-8.*
Muller et al., "Isotope-tagged cross-linking reagents. A new tool in mass spectrometric protein interaction analysis." Anal. Chem., 2001, 73, 1927-34.*
Pearson et al., "Intramolecular cross-linking experiments on cytochrome c and ribonuclease A using an isotope multiplet method." Rapid Comm. Mass Spectrom., 2002, 16, 149-59.*
Taverner et al., "Characterization of an antagonist interleukin-6 dimer by stable isotope labeling, cross-linking, and mass spectrometry." J. Biol. Chem., 2002, 277, 46487-92.*
Back et al. "Identification of cross-linked peptides for protein interaction studies using mass spectrometry and 18O labeling." Anal. Chem., 2002, 74, 4417-22.*
Back et al. "A new crosslinker for mass spectrometric analysis of the quaternary structure of protein complexes." J. Am. Soc. Mass. Spectrom., 2001, 12, 222-7.*
Tang et al., Mass Spectrometry Identifiable Cross-Linking Strategy for Studying Protein—Protein Interactions, Anal. Chem. 77:311-318, 2005.
Rink, H. Tetrahedron Lett. 28:3787-3790, 1987.
Zhou, H. et al., Nature Biotechnology 19:512-515, 2002.

* cited by examiner

*Primary Examiner*—Cecilia Tsang
*Assistant Examiner*—Christina Marchetti Bradley
(74) *Attorney, Agent, or Firm*—Barry L. Davison; Davis Wright Tremaine LLP

(57) ABSTRACT

Particular aspects provide novel protein interaction reporter (PIR) compounds (e.g., formulas I and II), comprising at least two protein reactive moieties (e.g., N-hydroxysuccinamide), each linked to a reporter moiety (e.g., mass reporter) by a covalent labile bond that is differentially cleavable with respect to peptide bonds (e.g., by a method such as collisional activation in a mass spectrometer, activation by electron capture dissociation (ECD), photoactivation, etc.), wherein the reporter moiety is operatively releasable from the PIR agent upon cleavage of the labile bonds, the released reporter moiety having a characteristic identifying property or label (e.g., m/z value). Particular PIRs comprise a mass reporter moiety, and further comprise an affinity group, (e.g., biotin), linked to the PIR (e.g., to the mass reporter moiety) by a selectively cleavable bone (e.g. photo-labile bond)). Additional aspects provide methods for characterizing intermolecular or intramolecular protein interactions using one or more inventive PIR compounds.

24 Claims, 18 Drawing Sheets

S-peptide  $^{01}$<u>K</u>ETAAAKFERQHMDSSTSAA

S-protein  $^{01}$SSSNYCNQMMKSRNLT<u>K</u>DRCKPVNTFVHES
$^{31}$LADVQAVCSQKNVACKNGQTNCYQSYSTMS
$^{61}$ITDCRETGSSKYPNCAYKTTQANKHIIVAC
$^{91}$EGNPYVPVHFDASV

SEQUENCE LISTING

<160> NUMBER OF SEQ ID NOS: 6

<210> SEQ ID NO 1
<211> LENGTH: 6
<212> TYPE: PRT
<213> ORGANISM: Artificial Sequence
<220> FEATURE:
<223> OTHER INFORMATION: RNase S peptide

<400> SEQUENCE: 1

Asn Leu Thr Lys Asp Arg
 1               5

<210> SEQ ID NO 2
<211> LENGTH: 20
<212> TYPE: PRT
<213> ORGANISM: Bos taurus

<400> SEQUENCE: 2

Lys Glu Thr Ala Ala Ala Lys Phe Glu Arg Gln His Met Asp Ser Ser
 1               5                  10                  15

Thr Ser Ala Ala
            20

<210> SEQ ID NO 3
<211> LENGTH: 104
<212> TYPE: PRT
<213> ORGANISM: Bos taurus

<400> SEQUENCE: 3

Ser Ser Ser Asn Tyr Cys Asn Gln Met Met Lys Ser Arg Asn Leu Thr
 1               5                  10                  15

Lys Asp Arg Cys Lys Pro Val Asn Thr Phe Val His Glu Ser Leu Ala
            20                  25                  30

Asp Val Gln Ala Val Cys Ser Gln Lys Asn Val Ala Cys Lys Asn Gly
            35                  40                  45

Gln Thr Asn Cys Tyr Gln Ser Tyr Ser Thr Met Ser Ile Thr Asp Cys
        50                  55                  60

Arg Glu Thr Gly Ser Ser Lys Tyr Pro Asn Cys Ala Tyr Lys Thr Thr
65                  70                  75                  80

Gln Ala Asn Lys His Ile Ile Val Ala Cys Glu Gly Asn Pro Tyr Val
                85                  90                  95

```
Pro Val His Phe Asp Ala Ser Val
            100

<210> SEQ ID NO 4
<211> LENGTH: 19
<212> TYPE: PRT
<213> ORGANISM: Bos taurus

<400> SEQUENCE: 4

Lys Glu Thr Ala Ala Ala Lys Phe Glu Arg Gln His Met Asp Ser Ser
 1               5                  10                  15

Thr Ser Ala

<210> SEQ ID NO 5
<211> LENGTH: 11
<212> TYPE: PRT
<213> ORGANISM: Artificial Sequence
<220> FEATURE:
<223> OTHER INFORMATION: Sub P peptide

<400> SEQUENCE: 5

Arg Pro Lys Pro Gln Gln Phe Phe Gly Leu Met
 1               5                  10

<210> SEQ ID NO 6
<211> LENGTH: 7
<212> TYPE: PRT
<213> ORGANISM: Bos taurus

<400> SEQUENCE: 6

Lys Glu Thr Ala Ala Ala Lys
 1               5
```

PROTEIN INTERACTION REPORTER AGENTS AND METHODS FOR USING SAME

CROSS-REFERENCE TO RELATED APPLICATIONS

This application claims the benefit of priority to U.S. Provisional Patent Application Ser. No. 60/629,396, filed 18 Nov. 2004 and entitled CHEMICAL CROSS-LINKERS, METHODS OF USING CHEMICAL CROSS-LINKERS, AND METHODS FOR STUDYING PROTEIN-PROTEIN INTERACTIONS, which is incorporated by reference herein in its entirety.

STATEMENT REGARDING FEDERALLY-SPONSORED RESEARCH

This work was supported by U.S. Department of Energy Grant No. DE-FG02-04ER63924, and NIH grant No. S10 RR017805-01. The United States has certain rights in this invention, pursuant to 35 U.S.C. § 202(c)(6).

FIELD OF THE INVENTION

Particular aspects relate generally to protein or polypeptide cross-linking and methods for studying same, and more particularly to novel, substantially useful cross-linking compounds and methods for using same.

BACKGROUND

Many cellular functions are carried out through large multi-protein complexes, rather than individual proteins. The systematic mapping of proteome-wide protein interactions to produce a comprehensive network of protein-protein interactions, or 'interactome,' is thus essential for understanding processes in biological systems. However, characterization of protein interactions is challenging because most protein interactions are transient, and many are unstable. In addition, multi-protein complexes possess no common factors or physical properties that can be used as an analytical handle.

Nonetheless, numerous efforts have been undertaken to profile large-scale protein interaction networks within a given cell, as the study of protein-protein interactions is a critical component in systems biology research directed at characterizing complex network interactions and behavior to better enable comprehension of protein function. Two popular methods to study protein-protein interactions are: (i) the yeast two-hybrid system, which is a genetic approach; and (ii) the use of protein cross-linking in combination with mass spectrometry (MS) to analyze purified protein complexes as well as their topological structures.

Protein cross-linking approaches can, at least in principal, not only identify what proteins interact within a complex, but can also pinpoint where proteins interact. However, despite much interest in profiling protein-protein interactions using cross-linking strategies and the availability of many commercial cross-linkers, (see, e.g., Pierce Chemicals, Double-Agents Cross-Linking Guide, 1999) few reports have illustrated progress in application/implementation of cross-linker approaches on a proteome-wide scale. This limitation is primarily due to inherent complexity in cross-linking reaction mixtures, which include large amounts of undesirable or unexpected products (see, e.g., Swaim, C. L. et al., *J Am Soc Mass Spectrom* 15:736-749, 2004), in addition to 1:1 linkage of interacting proteins. Moreover, the challenge of interpreting cross-linking approach results derives not only from the complexity of cross-linking reaction and digestion mixtures, but also from the complexity of MS/MS mass spectra—typically used for investigation of cross-linked peptides.

Therefore, there is a pronounced need in the art for novel cross-linking agents, and methods for using such agents, to simplify the identification and characterization of cross-linked proteins and peptides and thus facilitate the viability and utility of mass spectrometry for effective 'interactome' characterization.

SUMMARY

Particular aspects provide novel multivalent protein interaction reporter (PIR) compounds, and methods for using same (e.g., mass spectrometry-based methods, etc., as described in the working examples herein).

Additional aspects provide novel protein interaction reporter (PIR) compounds having formulas I or II:

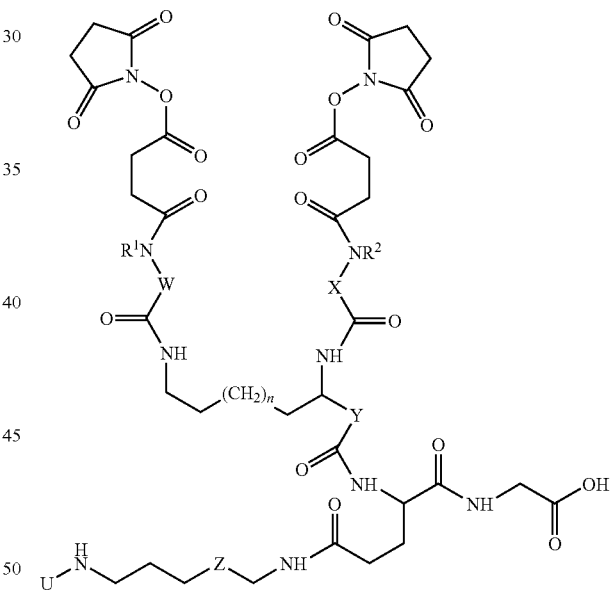

where R1, R2, W, X, Y, Z and U are as defined herein below.

The inventive PIR compounds comprise at least two protein reactive moieties (e.g., N-hydroxysuccinamide), each linked to a reporter moiety (e.g., mass reporter) by a covalent labile bond that is differentially cleavable with respect to peptide bonds (e.g., by a method such as collisional activation in a mass spectrometer, activation by electron capture dissociation (ECD), photoactivation, etc.), wherein the reporter moiety is operatively releasable from the PIR agent upon cleavage of the labile bonds, the released reporter moiety having a characteristic identifying property or label (e.g., m/z value). Particular PIRs comprise a mass reporter moiety, and further comprise an affinity group, (e.g., biotin), linked to the PIR (e.g., to the mass reporter moiety) by a selectively cleavable bone (e.g. photo-labile bond)).

Additional aspects provide a method of characterizing intermolecular or intramolecular protein interactions, comprising: obtaining a sample comprising at least one protein; contacting the at least one protein with at least one multivalent protein interaction reporter (PIR) compound, under conditions suitable for cross-linking to provide a cross-linked protein sample, wherein the PIR compound comprises at least two protein reactive moieties, each bound to a shared characteristic reporter moiety by a covalent labile bond, wherein the labile bonds can be differentially cleaved with respect to peptide bonds, wherein the reporter moiety is operatively releasable from the PIR agent upon differential cleavage of the labile bonds to provide for a characteristic released reporter moiety; differentially cleaving the labile bonds to provide for a released reporter moiety; and subjecting the cleaved products to an analysis suitable to distinguish the cleavage products by virtue of being the reporter moiety or by inclusion of a protein reactive moiety or portion thereof, wherein characterizing intermolecular or intramolecular protein interaction or structure is, at least in part, afforded. In particular aspects, the method of further comprises digesting, prior to differential bond cleavage, the cross-linked protein sample with at least one protease.

DETAILED DESCRIPTION

Figure 1:
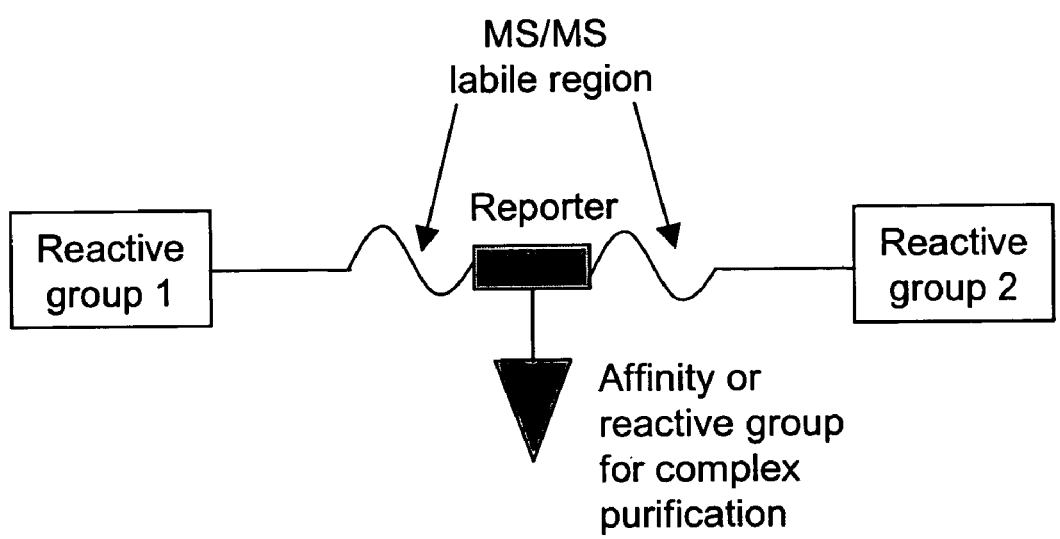
FIG. 1 shows a conceptual modular design of novel cross-linkers in accordance with particular aspects of the present invention.

Particular aspects relate to compositions and methods having substantial utility for characterizing inter-molecular or intra-molecular protein interactions or structures, utilizing novel multivalent protein interaction reporter (PIR) compounds. Certain embodiments relate to methods comprising use of PIR compounds to cross-link proteins or peptides, followed by subsequent analysis by mass spectrometry (MS). Upon exposure to a sufficient amount of activation energy in a mass spectrometer, PIR compounds undergo labile bond cleavage that produces a characteristic reporter ion with a distinct, identifiable mass to charge (m/z) ratio. The reporter ion serves to identify fractions that have cross-linked peptides, even where such fractions are present as a small percentage of a large, complex mixture of proteins and cross-linkers. Generally, the amount of energy required to release the reporter ion is lower than the amount of energy required to break a peptide bond. Following the release of the reporter ion, the peptides that were cross-linked by an inventive PIR compound may be subjected to one or more additional rounds of MS to determine the identity and/or sequence of the peptide.

Exemplary PIR compounds (FIG. 1) are multi-component molecules, comprising at least two protein reactive groups, at least two cleavage groups having covalent labile bonds, a characteristic mass-reporter group ('reporter group'), and an optional affinity tag that may be removable from the rest of the PIR, by cleavage an additional optional cleavage group there-between. PIR compounds have substantial utility to cross-link proteins and/or peptides. As used herein, the term "PIR agent" or "PIR composition" refers to a composition comprising one or more PIR compounds.

The at least two protein reactive groups may be identical or different, and are chemical moieties that form covalent links with proteins and/or peptides. Certain embodiments of the invention utilize an N-hydroxysuccinamide (NHS) ester as a protein reactive group. NHS esters generally react with amine groups of proteins or peptides. Other examples of protein reactive groups encompassed herein include aryl azides (react with primary amines), carbodiimides (react with amines or carboxyls), hydrazide (reacts with carbohydrates), hydroxymethyl phospine (reacts with amines), imidoesters (react with amines), isocyanates (react with hydroxyls), maleimides (react with sulfhydryls), PFP esters (react with amines), psoralen (a photoreactive intercalator that reacts with thymine), vinyl sulfones (react with sulfhydryls, amines, and hydroxyls), and pyridyl disulfides (react with sulfhydryls).

Inventive PIR compounds may have two or more protein reactive groups. Inventive PIR compounds are referred to as "multivalent," because PIR compounds may form cross-links with more than one protein or peptide. Additionally, the protein reactive groups in a single PIR compound may all be the same, or alternatively, two or more different protein reactive groups may be present in a single PIR compound. It will be apparent to one of ordinary skill in the art that the choice of protein reactive groups may be strategically selected for particular purposes, and the results compared between and among analyses using different protein reactive groups.

"Cleavage groups" refer to regions of the inventive PIR compounds that comprise a labile covalent bond, cleavable under appropriate conditions to separate the protein reactive groups from the mass reporter group, which is situated between two protein reactive groups. Generally, cleavage groups are located between the protein reactive groups and the reporter group. As used herein, the term "labile covalent bond" refers to a bond that may be broken under conditions that generally do not result in the breaking of peptide bonds.

Certain embodiments of the invention comprise cleavage groups that are "MS-labile". MS-labile bonds are bonds that generally break during mass spectrometry conditions wherein relatively low activation energy is used. Under these conditions, the inventive PIR molecules fragment at the cleavage groups (at the labile bonds), while the peptide bonds of the cross-linked proteins generally remain intact.

Chemical moieties that may be used as cleavage groups in PIR compounds include, but are not limited to N-functionalized heterocyclic aromatic compounds, such as substituted or unsubstituted indole or pyridyl-based compounds, secondary and tertiary amines wherein one bond is to a carbon atom neighboring group with significant π-delocalization, such as substituted biphenyl compounds, dithiols, phosphates, and metal ligand complexes. For PIR compounds having more than one cleavage group, the cleavage groups may all be the same, or they may be different (e.g., two or more different cleavage groups.

Figures 11A, 11B, 11C:
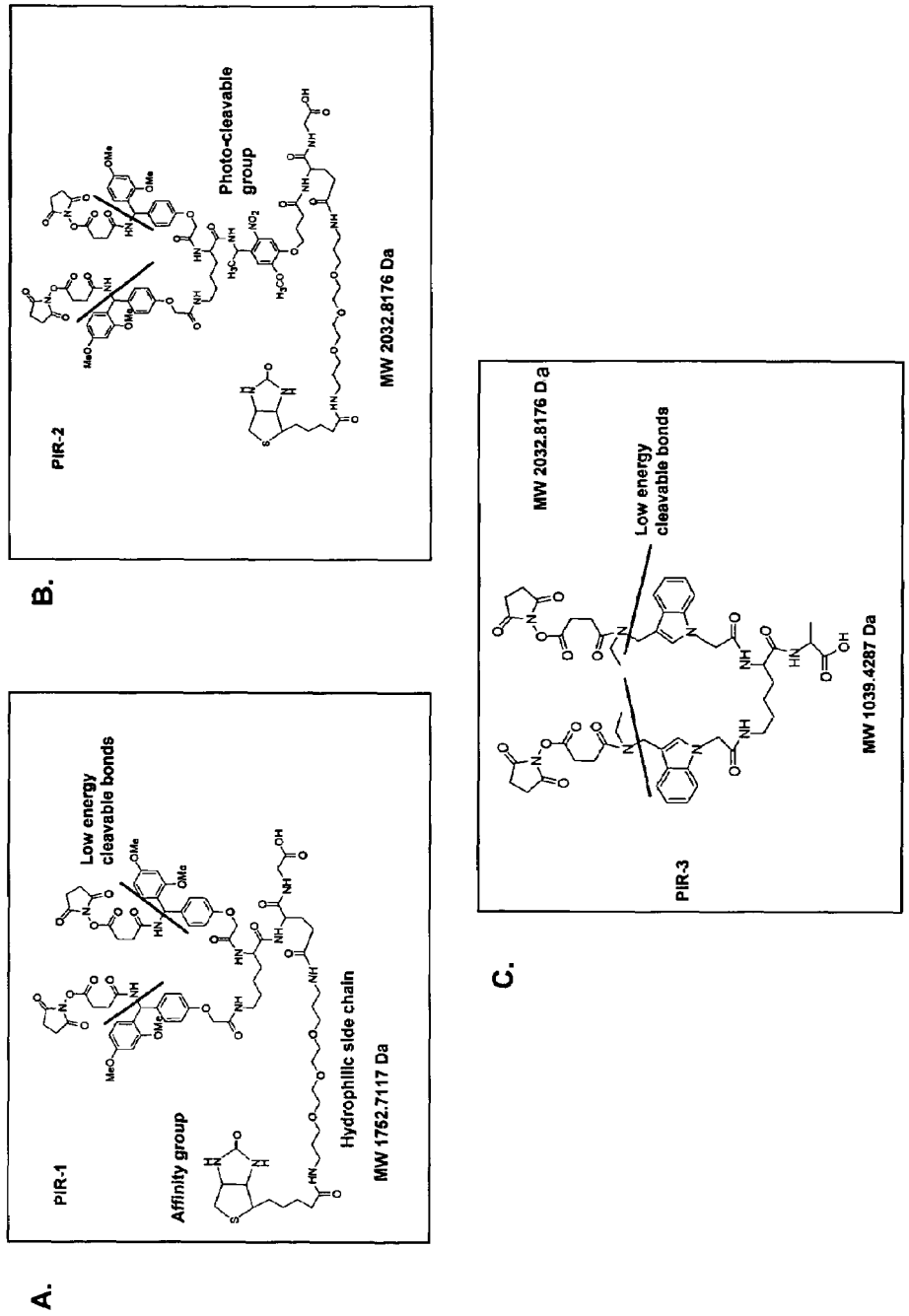
FIG. 11A shows the chemical structure of PIR-1 in accordance with an embodiment of the present invention. For PIR-1, a hydrophilic group ("Hydrophilic side chain") was introduced, along with Biotin ("Affinity group"), as an affinity support for sample enrichment. N-hydroxysuccinamide was used as reactive groups. Low energy MS/MS cleavable bond positions are shown with lines. ("Low energy cleavable bonds"). The molecular weight of PIR-1 is 1752.7117 Da. After reaction and MS/MS fragmentation, a 'tag mass' of 100.0399 Da was added to the cross-linked peptide for PIR-1.
FIG. 11B shows the chemical structure of PIR-2 in accordance with an embodiment of the present invention. Relative to PIR-1, a photo-cleavable group ("Photo-cleavable group") was introduced in PIR-2. N-hydroxysuccinamide was used as reactive groups. The molecular weight of PIR-2 is 2032.8176 (mono isotopic mass). After reaction and MS/MS fragmentation, a 'tag mass' of 100.0399 Da was added to the cross-linked peptide for PIR-2.
FIG. 11C shows the chemical structure of PIR-3 in accordance with an embodiment of the present invention. Relative to PIR-1 and PIR-2, PIR-3 comprises a distinguishing acid cleavable group (3-{ethyl-Fmoc-amino]-methyl}-indol-1-yl)-acetic acid, and was synthesized with no affinity support. Alternatively, PIR-3 can be constructed with an analogous affinity support with analogous peptide synthesis chemistry. The molecular weight of PIR-3 is 1039.4287 Da. N-hydroxysuccinamide was used as reactive groups. After reaction and MS/MS fragmentation, a 'tag mass' of 128.0712 Da was added to the cross-linked peptide for PIR-3.

Certain embodiments of the invention relate to the use of "Rink" or Rink-related compounds as cleavage groups. The term "Rink" refers to a trialkoxy-diphenyl-methylester disclosed by Rink et al. (see, e.g., Rink, H.; *Tetrahedron Lett.* 28:3787-3790, 1987). Additionally, U.S. Pat. No. 5,124,478 (incorporated herein by reference in its entirety) discloses a number of Rink-related compounds that have MS-labile bonds and may be useful as cleavage groups of the inventive PIR compounds. Additional embodiments of the invention comprise indole-based MS-labile cleavage groups. FIG. 11C shows a PIR compound with an indole-based cleavage group ("PIR-3").

The reporter group of a PIR compound may also be referred to as a "central mass reporter moiety," and is a region of the molecule in between the cleavage points defined by the cleavage groups. Generally, when labile covalent bonds are broken at both cleavage groups, a reporter group is released. The reporter group, upon release from the PIR compound, has a characteristic property that identifies it as the reporter group (e.g., a characteristic m/z value, etc.).

PIR compounds may further comprise an affinity group or tag that is covalently linked to the reporter group (e.g., via a connector region or arm). Such affinity tags may be used to react with or bind to a recognition element, which may be free in solution or immobilized on a solid. The affinity tag may be used to at least partially separate PIR compounds which may be cross-linked to peptides or proteins from other proteins that are not cross-linked to PIR compounds. Certain embodiments of the invention comprise biotin as an affinity tag that is attached to a reporter group (e.g., via an hydrophilic connector arm). Other affinity tags or reactive groups useful for this purpose include, but are not limited to poly histidine (4-14, preferably 6-10 residues), antibodies or antigens, benzophenone, sulfhydryl groups, and substituted or unsubstituted aryl azide. Examples of affinity capture components include, but are not limited to biotin and avidin, an antibody and an antigen, an aptamer and a small molecule, a polyhistidine tag and nickel, and a reactive group such as a thiol, which can undergo a Michael addition.

The connector region or arm between the affinity group and the reporter group may vary depending on the proposed application of the PIR compound. The connector regions or arms may vary in length, and, for example, may be hydrophobic or hydrophilic. Hydrophilic connector regions or arms may be selected to promote solubility and facilitate interactions between proteins at their physiological pH. Certain embodiments of the invention provide connector regions or arms that are derived from polyethylene glycol. However, other connector regions or arms, such as hydrocarbons, or those containing ketones and esters are also suitable for inventive PIR cross-linkers.

PIR compounds may also comprise an additional cleavable group positioned between the reporter group and the affinity tag moiety. Preferably, cleavage of this additional cleavable group can be achieved selectively with respect to cleavage of the above-described at least two labile bonds (between the reporter and the protein reactive groups). This additional cleavage site may facilitate selective removal of the affinity tag from the rest of the PIR compound or from the reporter. Examples of compounds that may be useful for this cleavage site include photo-sensitive groups comprising bonds that break upon exposure to light of a certain wavelength. Zhou et al., for example, disclose the use of photo-activatable compounds that may be used as cleavable moieties (Zhou, H., et al., *Nature Biotechnology* 19:512-515, 2002; incorporated herein by reference in its entirety).

Particular embodiments provide for PIR compounds having formula I:

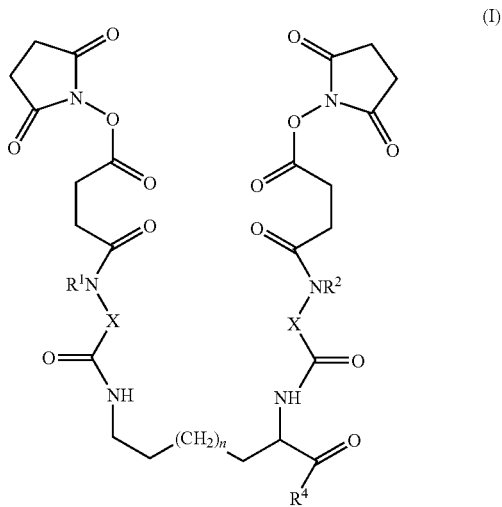

wherein: $R^1$ and $R^2$ are independently H, $CH_3$, or $CH_2$—$CH_3$; n=1-6;

wherein $R^4$ is hydroxyl, or

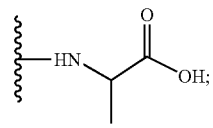

and wherein X is selected from the following:

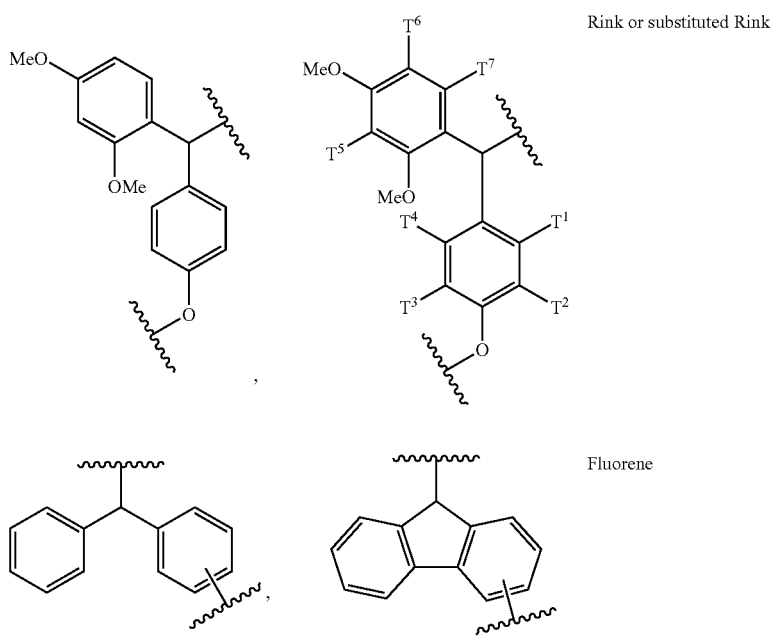

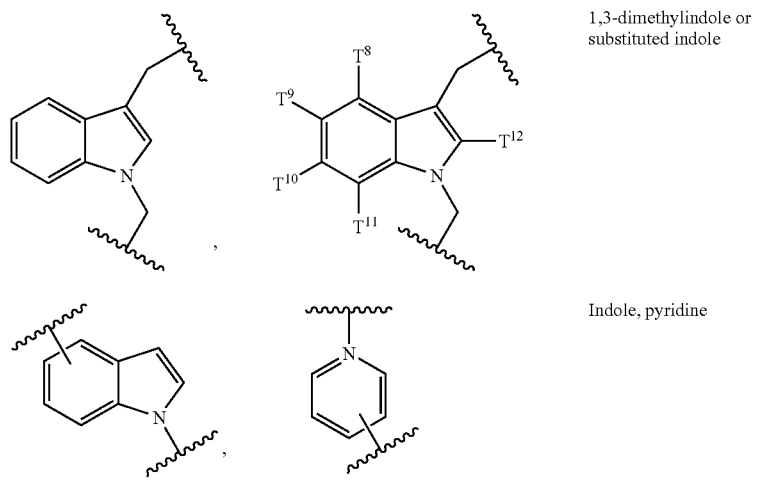

| | |
|---|---|
| | 1,3-dimethylindole or substituted indole |
| | Indole, pyridine | wherein $T^1$-$T^{12}$ are independently hydrogen, $(C_1$-$C_4)$-alkyl, or $(C_1$-$C_4)$-alkoxy; and wherein $R^3$ is H, $CH_3$, or $CH_2$—$CH_3$; wherein Q is O, N or S; wherein M is a transition metal (e.g., Zn, Fe, Co, Cu, Mn, Ni, Cr, Cd, etc);

Particular embodiments provide a compound of formula I, wherein X is:

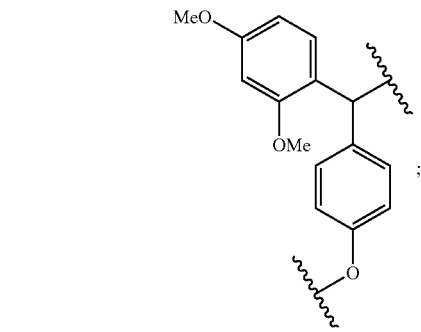

and wherein $R^4$ is hydroxyl.

Additional embodiments provide a compound of formula I, wherein X is:

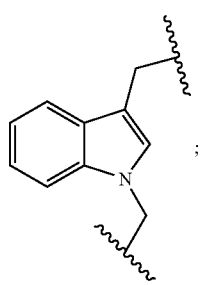

and wherein $R^4$ is

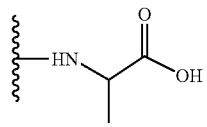

Further embodiments provide for PIR compounds having formula II:

(II)

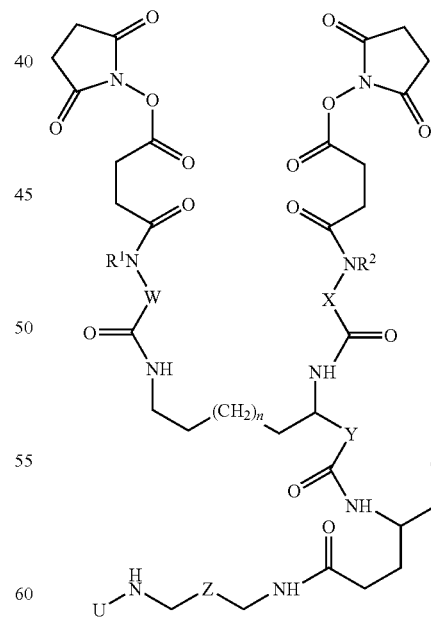

wherein $R^1$ and $R^2$ are independently selected from hydrogen, or $(C_1$-$C_4)$-alkyl;

wherein: n=1-6; and W and X are independently selected from:

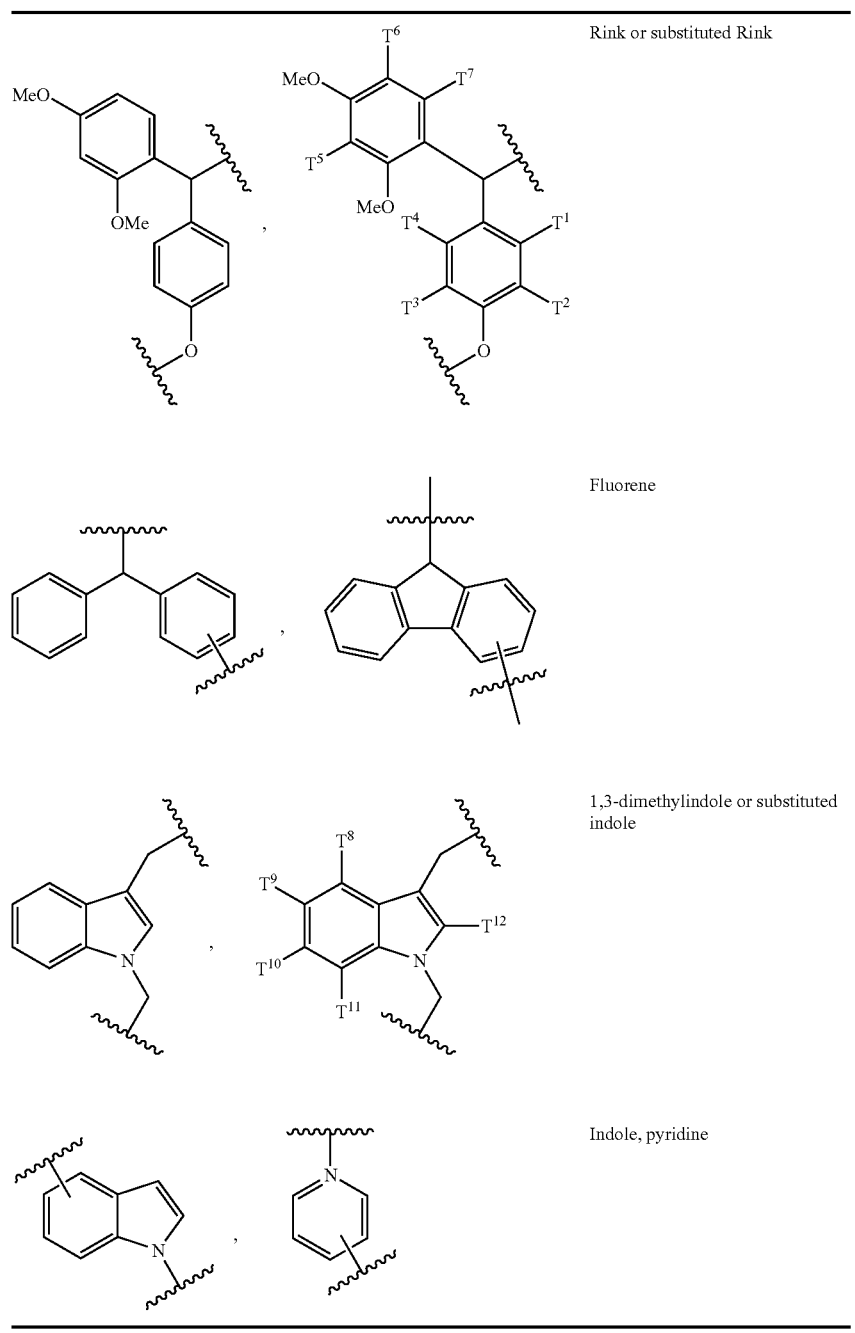
wherein $T^1$-$T^{12}$ are independently hydrogen, $(C_1$-$C_4)$-alkyl, or $(C_1$-$C_4)$-alkoxy;
wherein $R^3$ is H, $CH_3$, or $CH_2$—$CH_3$; wherein Q is O, N or S; wherein M is a transition metal (e.g., Zn, Fe, Co, Cu, Mn, Ni, Cr, Cd, etc);
wherein Y is nothing or
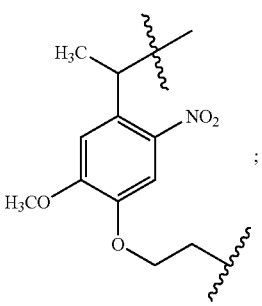

wherein Z is: $(-CH_2-CH_2-O-)_m$; $(-CH_2-)_q$; $(-CO-CH_2-)_r$; $(-CH_2-CO_2-)_r$; $(-CH_2-CO-CH_2-CO_2-)_s$, where m=1-5, q=5-15, r=3-7 and s=1-4 (as shown in the table below)

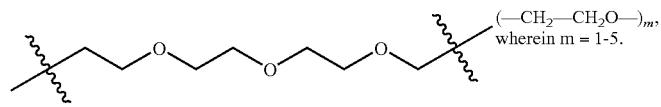
$(-CH_2-CH_2O-)_m$, wherein m = 1-5.

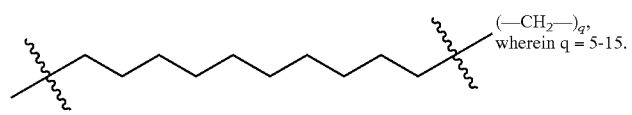
$(-CH_2-)_q$, wherein q = 5-15.

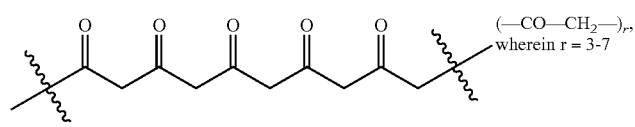
$(-CO-CH_2-)_r$, wherein r = 3-7

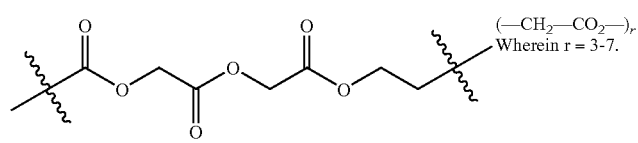
$(-CH_2-CO_2-)_r$ Wherein r = 3-7.

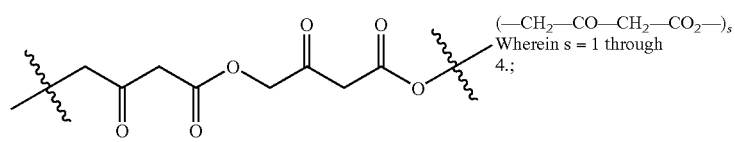
$(-CH_2-CO-CH_2-CO_2-)_s$ Wherein s = 1 through 4.;

and wherein U is biotin, poly-histidine (6-10 residues), benzophenone (formula IV), sulfhydryl, or aryl azide (formula V).

formula IV

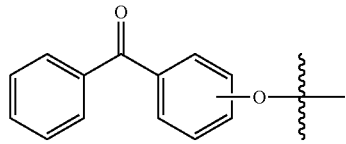

formula V

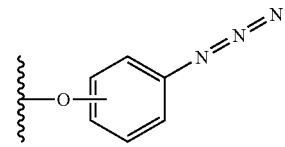

Particular embodiments provide a compound of formula II, wherein W and X are

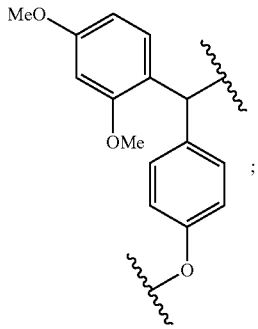

wherein Y is nothing; wherein Z is: $(-CH_2-CH_2-O-)_m$, where m=3; and wherein U is

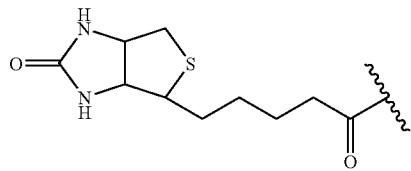

Additional embodiments provide a compound of formula II, wherein W and X are

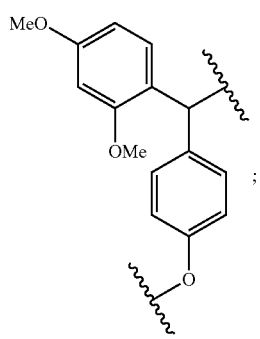

wherein Y is

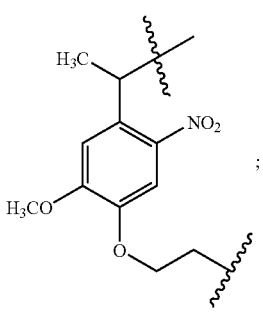

wherein Z is: (—CH$_2$—CH$_2$—O—)$_m$, where m=3; and
wherein U is

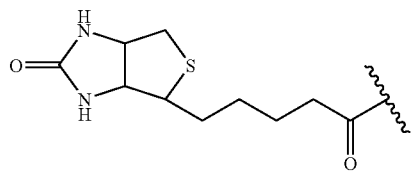

Additional embodiments provide a compound of formula II, wherein W and X are

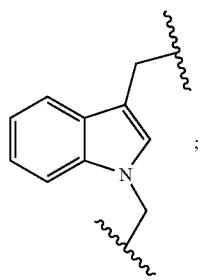

wherein Y is nothing; wherein Z is: (—CH$_2$—CH$_2$—O—)$_m$, where m=3; and wherein U is

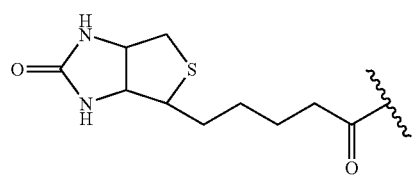

Further embodiments provide a compound of formula II, wherein W and X are

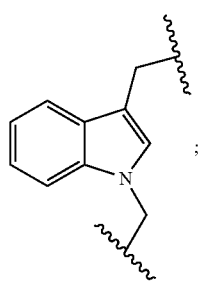

wherein Y is

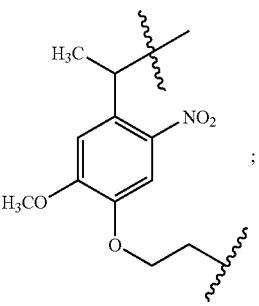

wherein Z is: (—CH$_2$—CH$_2$—O—)$_m$, where m=3; and wherein U is

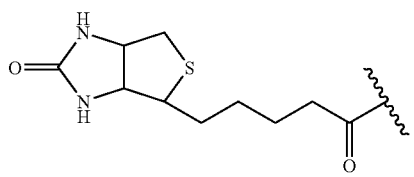

Preferably, the compounds of formula II are of formula III:

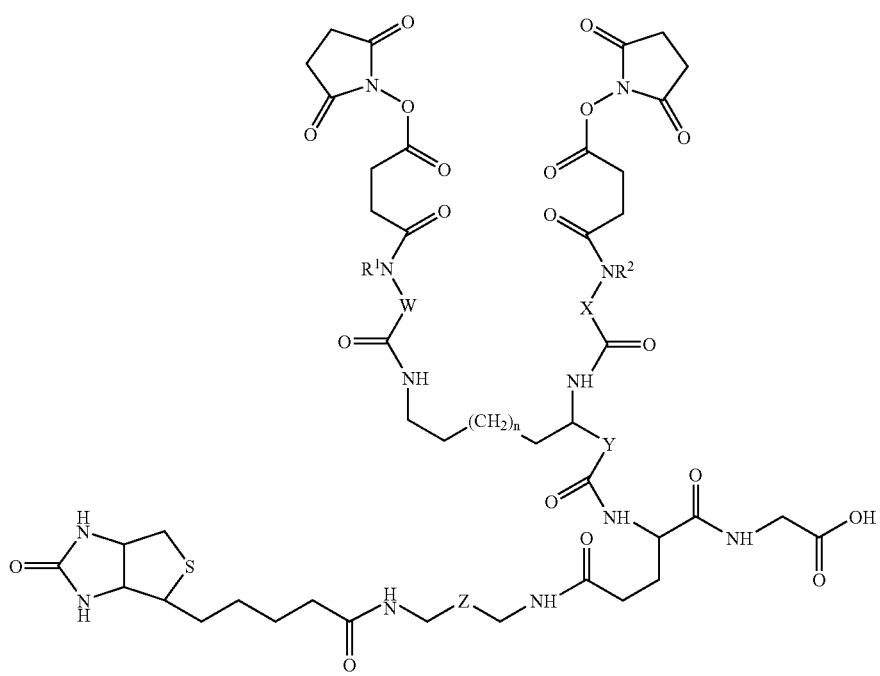

wherein $R^1$, $R^2$, W, X, Y and Z are as defined above with respect to formula II.

Particular aspects provide a multivalent protein interaction reporter (PIR) compound, comprising two protein reactive moieties, each linked to a shared reporter moiety (e.g., mass reporter moiety) by a covalent labile bond that is differentially cleavable with respect to peptide bonds (e.g., by a method selected from the group consisting of collisional activation in a mass spectrometer, activation by electron capture dissociation (ECD), photoactivation and combinations thereof), wherein the reporter moiety is operatively releasable from the PIR agent upon cleavage of the labile bonds, the released reporter moiety having a characteristic identifying property or label (e.g., m/z value).

In preferred aspects, the protein interaction reporter (PIR) comprises a mass reporter moiety, and further comprises (e.g., attached to the reporter moiety) an affinity group to allow for affinity purification of the PIR compound. Preferably, the affinity group is linked to the mass reporter moiety by a selectively cleavable bone (e.g. photo-labile bond), to enable selective detachment of the affinity group from the PIR compound. In particular embodiments, the affinity group comprises a moiety selected from the group consisting of biotin, poly histidine (6-10 residues), benzophenone, sulfhydryl, aryl azide and combinations thereof. Preferably, the affinity group comprises biotin.

In particular embodiments, the protein reactive moieties comprise N-hydroxysuccinamide.

In particular embodiments, the mass reporter moiety comprises one or both of

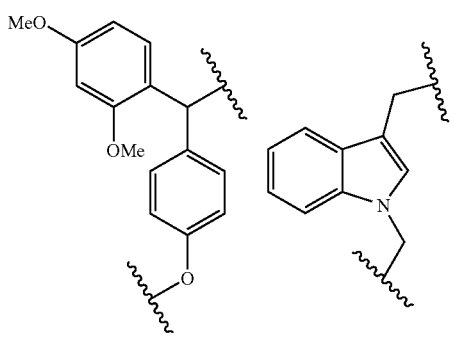

In preferred embodiments, the protein interaction reporter (PIR) compound is of formula I or formula II disclosed herein:

Additional aspects provide a method of characterizing intermolecular or intramolecular protein interactions, comprising: obtaining a sample comprising at least one protein; contacting the at least one protein with at least one multivalent protein interaction reporter (PIR) compound, under conditions suitable for cross-linking to provide a cross-linked protein sample, wherein the PIR compound comprises at least two protein reactive moieties, each bound to a shared characteristic reporter moiety by a covalent labile bond, wherein the labile bonds can be differentially cleaved with respect to peptide bonds, wherein the reporter moiety is operatively releasable from the PIR agent upon differential cleavage of the labile bonds to provide for a characteristic released reporter moiety; differentially cleaving the labile bonds to provide for a released reporter moiety; and subjecting the cleaved products to an analysis suitable to distinguish the cleavage products by virtue of being the reporter moiety or by inclusion of a protein reactive moiety or portion thereof, wherein characterizing intermolecular or intramolecular protein interaction or structure is, at least in part, afforded.

In particular aspects, the method of further comprises, prior to differential bond cleavage, digesting the cross-linked protein sample with at least one protease.

In certain embodiments, the characteristic reporter moiety is a mass reporter moiety having a characteristic m/z value, the mass reporter moiety bound to each protein reactive moiety by a labile bond that is differentially cleavable with respect to peptide bonds by a method selected from the group consisting of collisional activation in a mass spectrometer, activation by electron capture dissociation (ECD), photoactivation and combinations thereof, and wherein subjecting the cleaved products to an analysis suitable to distinguish the cleavage products is, at least in part, by mass spectrometry.

In particular embodiments, differential cleavage of the labile bonds is by applying a first ms activation energy sufficient to provide for a released mass reporter moiety having a characteristic m/z value, and to provide for a released polypeptide or peptide linked to a protein reactive moiety or portion thereof having a characteristic m/z value. In additional aspects, the method further comprises subjecting at least one cleaved product to a second, higher ms activation energy sufficient to fragment peptide bonds.

Preferably, in such methods, the protein interaction reporter (PIR) compound is a compound of formula I or formula II as defined herein.

In yet further embodiments, the inventive methods comprise use of a plurality of distinguishable (e.g., having distinguishable protein reactive groups to provide for cross-linked products that can be independently analyzed, or otherwise analyzed) protein interaction reporter (PIR) compounds (e.g., of formula I or formula II as defined herein) to increase the sensitivity, utility and power of the methods for analysis of complex mixtures.

Inventive PIR compounds have substantial utility for the characterization of intermolecular or intramolecular protein interactions. As used herein, the term intermolecular protein interaction refers to interactions between two or more proteins or polypeptides. The term "intramolecular" protein interaction refers to interactions between different regions of an individual protein or polypeptide.

Characterization of a protein-protein interaction may occur by obtaining at least one protein and contacting the protein or proteins with a PIR agent under conditions suitable to cross-link the at least one protein with the PIR agent. The resulting mixture may contain inter, intra, and dead-end cross-linked species. Dead-end cross-linked species are cross-linking products wherein only one of the protein affinity groups are attached to a protein or polypeptide. This mixture may then be subjected to a condition, such as an activation energy, that results in cleavage of labile bonds of cleavage groups as described above, and attendant release of a characteristic reporter group.

Certain embodiments of the invention relate to conditions wherein the cross-linked species are subjected to a low-energy MS activation step that fragments the cross-linked species at the labile bonds of the PIR cleavage groups, while leaving the peptide bonds of the cross-linked proteins or peptides largely intact. In this case, the released reporter group may be detected by a characteristic m/z value by mass spectrometry. Subsequent rounds of mass spectrometry may then be used to characterize the protein regions that have been released during the first round of mass spectrometry. In such subsequent rounds, peptide bonds may be fragmented to facilitate the identification or characterization (e.g., sequencing) of the polypeptides that were cross-linked by the PIR agent.

One method of activation for fragmentation and concomitant release of a reporter group from a PIR compound is collisional activation in a mass spectrometer. In general, polypeptides are fragmented by acceleration voltages greater than 20 V. The Rink-based and indole-based cleavage groups present in PIR compounds fragment with voltages less than 20 V. Performing collisional activation at less than about 20 V generally allows for the release of intact polypeptide/peptide ions from the PIR-labeled species. Under these conditions, it is possible to obtain an accurate mass value for the polypeptide/peptides to identify them, or the polypeptide/peptides can be individually fragmented for further identification or sequencing.

In other embodiments of the invention, fragmentation at cleavage groups may be induced by photoactivation. Photoactivation may be achieved in a mass spectrometer or within the capillary used for liquid introduction. The photolabile group may be cleaved without causing peptide fragmentation. An example of a compound that may be used as a photolabile cleavage group is described by Zhou et al. (Zhou, H., et al., *Nature Biotechnology* 19:512-515, 2002; incorporated herein by reference).

Further embodiments of the invention provide for activation by electron capture dissociation (ECD). Low energy (1-5 eV) electrons may be captured, for example, by trapped ions in a Fourier transform ion cyclotron resonance (FTICR) mass spectrometer, which is useful for peptide and protein sequence determination, because the resulting energy from charge recombination of electrons with multiply charged cations is available for backbone cleavage of peptides. ECD may be used with inventive PIRs to incorporate structures with high electron affinity that may more readily capture low energy electrons than peptides themselves. Thus, the ECD components of such PIRs will be fragmented with greater frequency than the polypeptides, leading to preferential PIR activation and peptide release.

One particularly advantageous feature demonstrated and provided herein is the capacity to distinguish dead-end and intra cross-linked peptides, and produce sequence information on peptides by combination of ECD and collisionally-activated dissociation (CAD). A useful feature of PIRs is that the mass of the reporter ion can be tuned by substituting different amino acids in the linker (e.g., spacer). The addition of an exemplary hydrophilic group and an exemplary photocleavable group was accomplished while maintaining the low energy fragmentation characteristics of the respective PIRs. The ability to distinguish dead-end, inter, and intra cross-linked peptides is a particularly useful feature of the instant reporter ion strategy, and provides for the effective use of the inventive cross-linkers (PIRs) in the field of interaction profiling for unambiguous identification and characterization of protein-protein interactions.

One embodiment of the present invention provides for the use of PIR compounds to cross-link a plurality of proteins present in a complex mixture, such as a cell extract or proteome. Proteins involved in protein-protein interactions vary greatly in their three-dimensional surface topography as well as in the chemical moieties present on their surfaces. To maximize the number or complexity of successful cross-linked products, a plurality of PIR compounds may be used together to characterize a variety of protein-protein interactions in a single cross-linking reaction.

Because different proteins exhibit different amino acid residues on their surface, it may be expedient to utilize multiple distinguishable PIR compounds having distinguishable protein reaction moieties; e.g., some having two or more identical protein reactive groups, and others having two or more different protein reactive groups. For example, PIR compounds having two identical protein reactive groups may be more efficient at cross-linking proteins that have similar reactive groups on their surfaces, while PIR compounds having two different protein reactive groups may facilitate the cross-linking of proteins that have different reactive groups on their surface.

Additionally, the distance between the reactive groups of proteins varies depending on the three-dimensional surface topography of the proteins forming the protein-protein complex. PIR compounds that vary in spacer arm length, for example, may promote cross-linking of proteins that vary in the distance between the amino acid chemical moieties that are reactive toward the PIR protein reactive groups.

Therefore, particular aspects provide methods comprising a plurality of different PIR compounds that vary in their protein reactive groups and/or their spacer arm lenghths, wherein the PIR compounds are contacted with a complex mixture of proteins. The population of cross-linked species may be enriched or purified by the virtue of an affinity group, and subsequently analyzed, for example, by mass spectrometry using methods as described and disclosed herein.

Example 1 below shows a new mass spectrometry identifiable cross-linking strategy that has been developed and validated with an exemplary inventive PIR cross-linker (Tang, X. et al., *Anal Chem* 77:311-318, 2005). This cross-linker was successfully synthesized and used herein to cross-link the RNase S complex. The presence of two Rink groups and a lysine residue in the spacer chain did not hinder the cross-linking reactivity of NHS groups. Low energy MS/MS of cross-linked peptides not only readily released the distinctive reporter ions allowing rapid screening of cross-linked peptides in complex mixtures, but also preserved intact peptide chains which allowed further fragmentation by additional ms stages (e.g., MS/MS, etc.).

The cross-linker of Example 1 was synthesized based on a peptide scaffold that makes the synthesis flexible and versatile for a variety of modifications. The development of new PIR cross-linkers with specific affinity and cleavage properties will ultimately facilitate profiling of proteome-wide protein-protein interactions.

Example 2 demonstrates three exemplary PIRs and their gas phase fragmentation characteristics in low energy, collision-induced dissociation (CID) experiments in Fourier transform ion cyclotron resonance mass spectrometry (FTICR-MS). Different fragmentation behavior of an intra-linked peptide in low energy CID and electron capture dissociation (ECD) was also demonstrated. These inventive PIRs displayed characteristic fragmentation in low energy CID experiments in FTICR-MS.

The compounds of Example 2 were constructed with acid-cleavable Rink and indole groups that have been found to fragment efficiently under low energy CAD. As shown and described herein, these groups can produce selective fragmentation of PIR labeled peptides in a low energy CID experiment in FTICR-MS. Additional features are incorporated into PIR compounds to improve the efficiency of cross-linking strategies. For example, hydrophilic groups, photo-cleavable groups, and other low energy MS/MS cleavable groups are incorporated into the inventive cross-linkers.

EXAMPLE 1

A New Mass Spectrometry Identifiable Cross-Linking Strategy for Studying Protein-Protein Interactions was Developed Chemicals. RNase S was purchased from Sigma (St. Louis, Mo.) and used without further purification. Fmoc-Rink, Fmoc-Lys (Fmoc)-OH, and HMPB-MBHA resins used for synthesis of cross-linker were purchased from Novabiochem (San Diego, Calif.). Sequencing grade modified trypsin was purchased from Promega (Madison, Wis.). Water used for preparing solution and solvent was 18 MΩ deionized water made by Barnstead Nanopure Water Systems.

Synthesis of Cross-Linker. The cross-linker PIR-0 (FIG. 2) was synthesized using standard methods, using a 431A Peptide Synthesizer (Applied Biosystem, Foster City, Calif.). Fmoc-Lys (Fmoc)-OH was coupled to HMPB-MBHA resin (4-hydroxymethyl-3-methoxyphenoxybutyric acid MBHA resin) using the standard symmetric anhydride method. Two Rink groups were coupled to Lys by treating the Fmoc-Rink linkers as Fmoc amino acid. Carboxyl groups were then introduced by reacting the primary amines of the Rink groups with succinyl anhydride. Subsequently, the two carboxyl groups were activated by forming the esters with N-hydroxysuccinimide (NHS). The final product was cleaved from the super acid sensitive resin with 0.5% TFA in chloroform. The purified final product was dissolved in DMSO to make 100 mM stock solution.

Cross-Linking Reaction. RNase S was dissolved in water to make 1 mM stock solution. For cross-linking reaction, 1 mM RNase S was diluted to 10 μM in phosphate saline buffer (100 mM sodium phosphate, 150 mM NaCl, pH 7.2) and the cross-linker was added in 50-, 100-, and 150-fold molar excess over RNase S. The reaction mixture was incubated at room temperature and an aliquot was taken at 15, 30, 60, and 120 min and quenched by 1 M Tris, pH 7.5 (final concentration 40 mM).

SDS-PAGE and In-Gel Digestion. An aliquot of each reaction mixture was loaded onto SDS-PAGE for separation by using precast 4-12% gel from Invitrogen (Carlsbad, Calif.). The gels were stained with Coomassie blue (Bio-Rad, Hercules, Calif.) and imaged by Densitometer (Molecular Dynamics). The gel bands of interest were excised and destained by 50% methanol and 5% acetic acid. Performic acid oxidation method was used to dissociate di-sulfide bonds of the proteins. Performic acid was freshly made by mixing 95/5 (v/v) formic acid/30% $H_2O_2$ and incubating the mixture at room temperature for 20 min followed by incubating on ice for 5 min. 20-30 μL performic acid was used to cover the gel pieces and oxidize proteins on ice for 1 hr. The gels were then washed and dried by acetonitrile. 20 ng/μL trypsin in 50 mM ammonium bicarbonate was used for digesting proteins at 37° C. (e.g., overnight).

Nano-LC/MS/MS and Data Analysis. An electrospray-ion trap (Esquire HCT, Bruker Daltonics, Billerica, Mass.) mass spectrometer coupled with a nano-HPLC was used for nano-LC/MS/MS analysis of cross-linked RNase S complex. Nano-HPLC separation of tryptic peptides was performed with an LC packings Ultimate Nano-HPLC system equipped with a Famos™ micro autosampler and a Swichos™ micro column switching module (Dionex, Sunnyvale, Calif.). Samples were first injected by the autosampler and loaded onto a micro trap column (C18 PepMap, 300 μm×1 mm, 5 μm, LC Packings) at a flow rate of 50 μL/min with solvent A (0.1% TFA in water). The loaded samples were continuously washed with solvent A for 3 minutes to remove salts. Peptides were then eluted at a flow rate of 300 nL/min on an analytical column (C18 PepMap, 75 μm×150 mm, 3 μm, 100 Å, LC Packings) and separated using the following gradient: 0% B for 0-3 min, 20-70% B for 3-45 min, 90% B for 45-55 min, and 0% B for 55-65 min. Solvent B was 0.1% TFA in 95% acetonitrile. The eluant from the analytical column was sprayed on-line with a nano-spray emitter to the Esquire HCT mass spectrometer. The nano-spray emitter was made by applicants by etching fused silica capillary (20 μm×360 μm) with HF. The spray potential was set at 1300-1500 volts. LC/MS/MS mass spectra were acquired using HyStar™ software (version 2.3, Bruker Daltonics). MS/MS data acquisition was set in automatic mode with active exclusion based on peak intensity and a selection of exclusion peak lists. Two precursor ions were selected from each MS scan and excluded after two MS/MS scans. $MS^3$ was performed manually by selecting specific precursor ions from MS/MS scan at specific retention time based on previous LC/MS/MS analysis of the same set of samples. For analysis of cross-linking reaction mixtures, samples were precipitated by TCA to remove the large amount of excessive unreacted cross-linker prior to loading to the nano-HPLC column. Calibration of the instrument was achieved using a solution of tuning mix (ES tuning mix, Agilent) composed of ions at m/z 322.05, 622.03, 922.01, 1521.93, and 2121.93. Data analysis and processing were performed using Bruker Daltonics Data Analysis software (version 3.1).

GPMAW™ software version 6.00 (Lighthouse Data, Odense, Denmark) was used to calculate the m/z of cross-linked peptides.

Results:

Cross-Linker Design and Synthesis. Despite great enthusiasm for using cross-linking approaches, successful reports for studying protein-protein interactions on a proteome-wide scale have been scarce, due in part to the complexity of mass spectral information and the need for additional cross-linker features. Desirable goals in developing mass spectrometry identifiable cross-linking strategies using the inentive PIR cross-linkers was to simplify MS/MS spectrum of cross-linked peptides and to guide data analysis by including a specific reporter.

The conceptual components of the chemistry development for the cross-linker reagents disclosed herein are shown in FIG. 1. Exemplary cross-linkers useful for such processes comprise low-energy mass spectrometry cleavable bonds which are more labile than peptide bonds, a feature that can significantly benefit spectral interpretation by allowing additional stages of MS/MS to be carried out. Mass measurement of the intact cross-linked species, followed by MS/MS analysis of each of the peptide chains will provide both the identities of cross-linked proteins, as well as information regarding sites of interaction.

In a particular embodiment, a Rink group was coupled to a 5-mer peptide and its specific cleavage property was tested by low energy MS/MS. As expected, a majority of the fragmentation occurred at the amine position between two phenyl groups in the Rink, and the peptide chain remained intact. This fragmentation was accomplished with activation energy significantly below that needed for peptide backbone fragmentation. Therefore, two Rink groups were used in this embodiment to provide two labile bonds for the inventive PIR cross-linker. According to preferred aspects, cleavage of the two labile bonds resulted in a specific reporter molecule as shown in FIGS. 1 and 2.

The exemplary cross-linker PIR-0 was made using solid phase Fmoc peptide synthesis chemistry. Two Rink groups were treated as amino acid analogs and coupled to two the primary amines in a lysine residue. Two N-hydroxysuccinimide (NHS) esters were subsequently incorporated to make the initial cross-linker. However, the proposed modular system can readily adapt new features by using different building blocks to incorporate an affinity tag or other functional groups as shown in FIG. 1. For example, a hetero-bifunctional cross-linker with one reactive group being NHS ester and the other one being benzophenone photoreactive group is encompassed within particular aspects.

Figure 2:
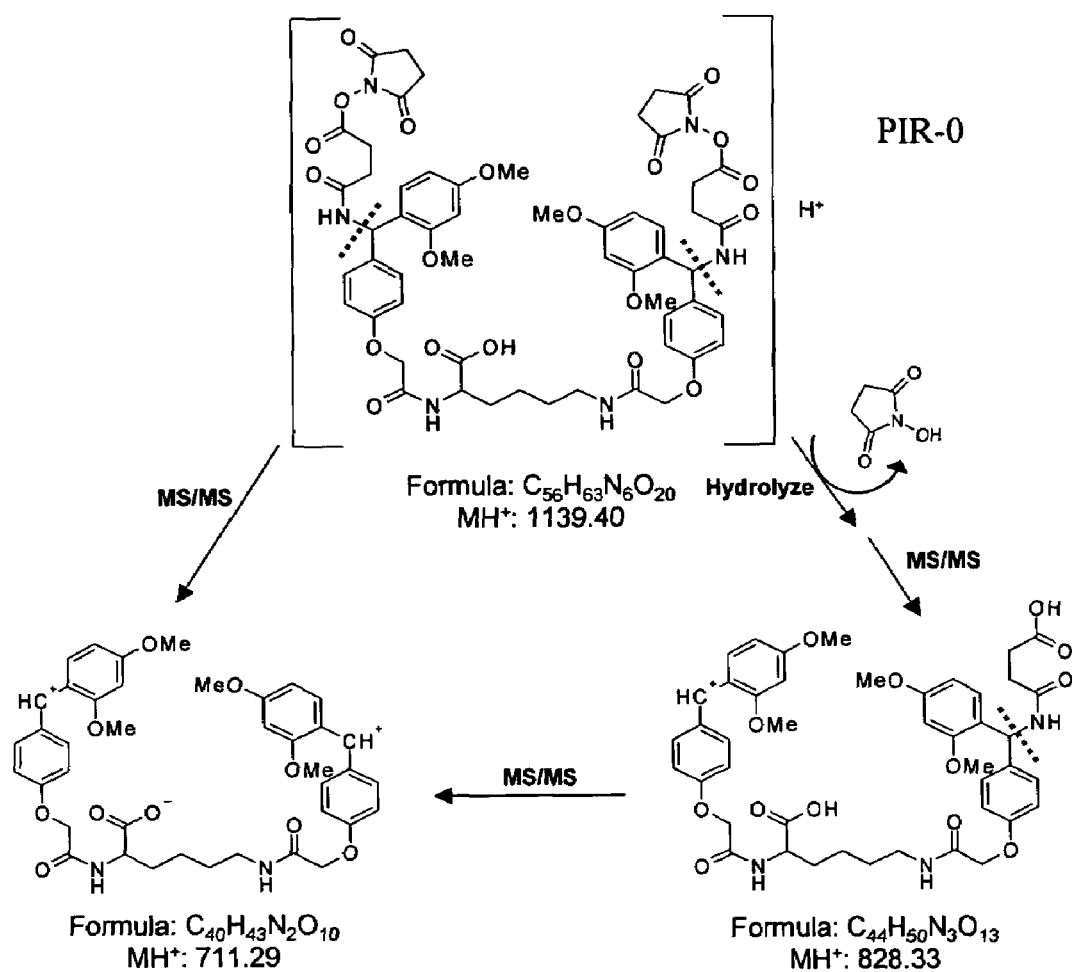
FIG. 2 shows an exemplary inventive cross-linker structure and representative reaction scheme. The dashed lines indicate labile bonds cleavable by low energy MS/MS, where cleavage of both labile bonds leads to the production of a characteristic reporter ion (e.g., at m/z 711). If one end of the cross-linker is hydrolyzed and then the labile bond on the other end is cleaved, a reporter ion at m/z 828 is generated.

FIG. 2 shows the structure of the inventive cross-linker PIR-0, and proposed reaction schemes. The MS/MS cleavage generally takes place at the amine bond between two phenyl groups in Rink as indicated by dashed lines in FIG. 2. The carbonyl cation ion formed after cleavage is delocalized among two phenyl groups and methoxy groups and thus highly stable. Further study showed that the cleavage of labile bonds usually took place by MS/MS in positive ion mode and generally not in negative ion mode, indicating protonation of parent compound was useful for desired fragmentation. Moreover, the same cleavage may occur if the compound is treated with 90% TFA, which is commonly used for peptide amide synthesis.

According to particular aspects, the acid cleavage feature can be used for tracking cross-links by comparing mass shift prior to and following cleavage of cross-links as any other cleavable cross-linkers such as DTSSP (Bennett, K. L. et al., *Protein Sci* 9:1503-1518, 2000; Back, J. W. et al., *Protein Sci* 11:2471-2478, 2002.) This feature was not used for the studies of this Example, because the mass spectrometric cleavage features of the cross-linkers provide more benefits. As shown in FIG. 2, if both vulnerable bonds in the cross-linker are cleaved, a reporter ion at m/z 711 is released and detected. This reporter ion may be used to track peptides that are either inter- or intra-cross-linked. If one end of the cross-linker is hydrolyzed and the labile bond on the other end is cleaved, as in the case of a peptide is dead-end modified, a reporter ion at m/z 828 will be detected. This reporter ion can be further cleaved to generate ion at m/z 711.

Figures 3A, 3B:
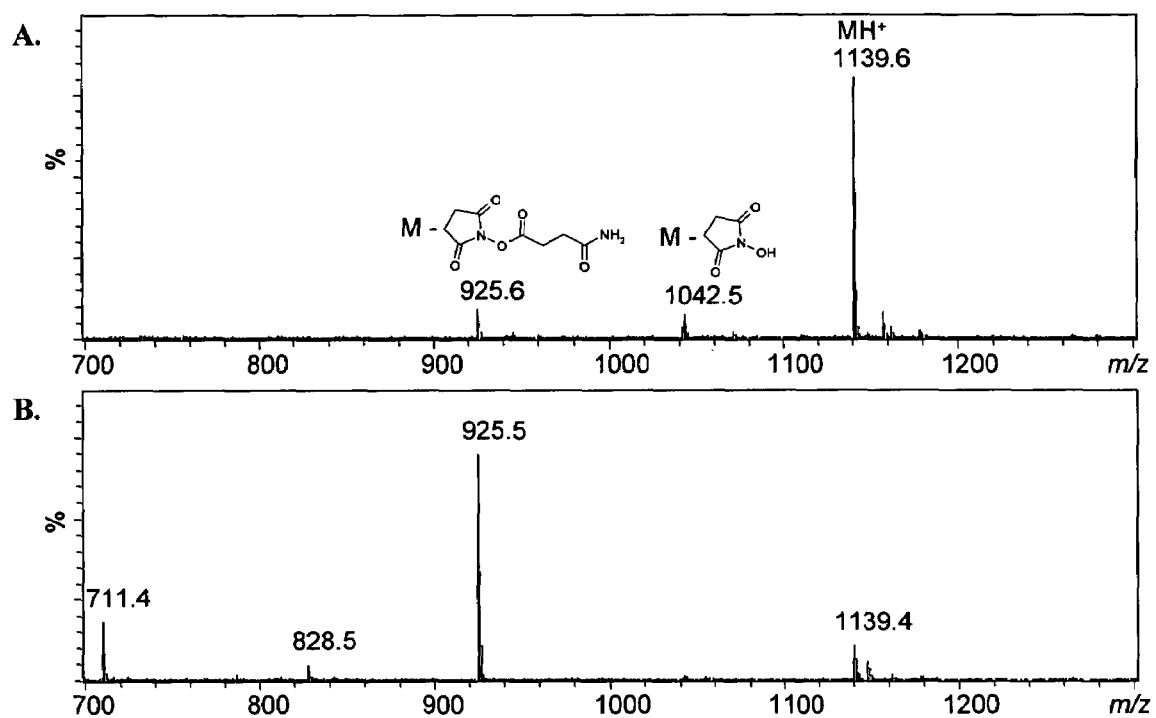
FIG. 3A shows an ESI mass spectrum of an inventive protein interaction reporter (PIR) cross-linker, acquired using low capillary exit voltage at 110 v. Most cross-linker remains intact as shown at m/z 1139.6.
FIG. 3B shows an ESI mass spectrum of a PIR cross-linker, acquired using high capillary exit voltage at 200 V. The cross-linker is fragmented by capillary exit and skimmer dissociation. Peaks, corresponding to reporter ions at m/z 828 and 711, were generated from the preferred cleavage of the labile bonds as indicated in FIG. 2.

To evaluate the cross-linker and its mass spectrometric dissociation properties, the purified final product was dissolved in acetonitrile to make a 10 μM solution that was directly infused to an ESI-ion trap mass spectrometer. FIG. 3 shows the mass spectra of the cross-linker. FIG. 3A shows that at low capillary exit voltage, the cross-linker remained mostly intact at m/z 1139.6. Some cross-linker was hydrolyzed at one end during electrospray process generating ions at m/z 1042.5. Ions at m/z 925.6 were the product from cleavage of one labile bond of the cross-linker. With increased capillary exit voltage, more cleavage was observed. As shown in FIG. 3B, reporter ions at m/z 711.4 and 828.5 resulting from activation in the region of capillary and skimmer were detected, indicating that the cross-linker may successfully release reporter ions under low energy MS/MS conditions.

Cross-Linking of RNase S Complex. Ribonuclease S(RNase S) is a complex of S-peptide 1-20 (SEQ ID NO:2) and S-protein 21-124 (redefined as 1-104; (SEQ ID NO:3)) (see FIG. 8) that are the hydrolysis products from ribonuclease A (RNase A) when RNase A is cleaved between residues 20 (Ala) and 21 (Ser) by subtilisin. S-peptide (SEQ ID NO:2) and S-protein (SEQ ID NO:3) have been found to form a weak non-covalent complex that retains similar enzymatic activity as RNase A. RNase S complex provides a useful model system for testing PIR cross-linkers.

The RNase S complex is believed to be heterogeneous; (Kirchner, M. et al., 52nd ASMS Conference on Mass Spectrometry and Allied Topics, Nashville, Tenn. 2004) other S-peptides and S-proteins were also found in the complex but only the first 15 residues of S-peptide are involved in non-covalent binding with S-protein (Wyckoff, H. W. et al., *J Biol Chem* 242:3749-3753, 1967). The RNase S used in this analysis was found to have S-peptides 1-20, 1-19, 1-18, 1-17, and 1-16; S-peptide 1-19 was most abundant. Nevertheless, RNase S was used as is without further purification.

Figure 4:
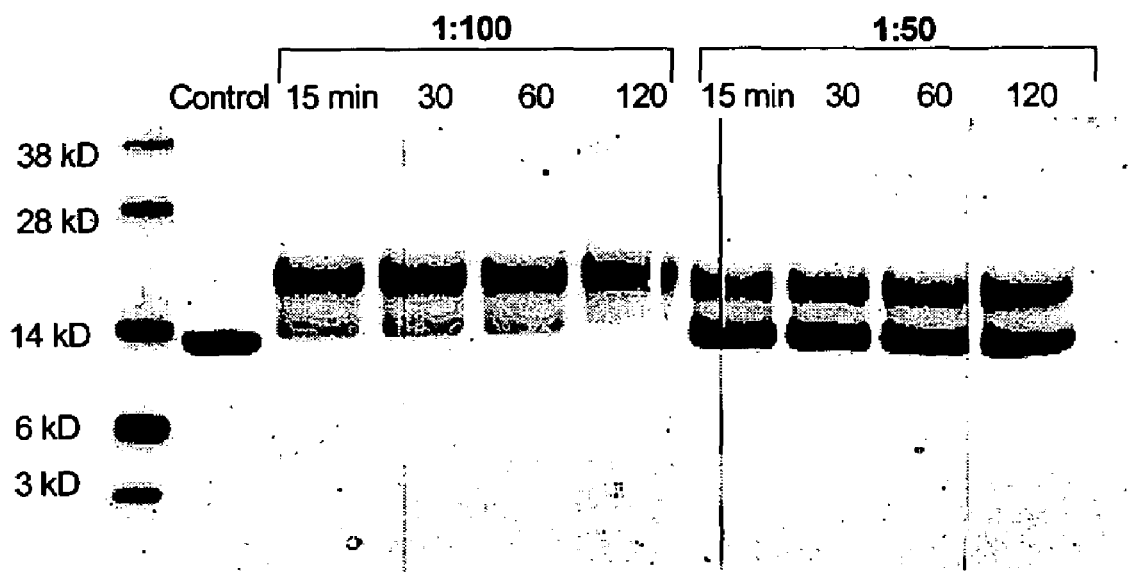
FIG. 4 shows SDS-PAGE analysis of cross-linking reaction mixtures with molar ratios of RNase S to cross-linker of 1:100 and 1:50, and cross-linking reaction times of 15, 30, 60, and 120 minutes. RNase S with no cross-linker was used as control.

Optimization of cross-linking conditions was carried out by varying molar ratios of RNase S to the cross-linker at 1:50, 1:100, and 1:150, and reaction time at 15, 30, 60, and 120 min for each reaction ratio. RNase S with no cross-linker added in the reaction buffer was used as a control. The resulting cross-linking reaction mixtures were separated by 4-12% SDS-PAGE followed by Coomassie blue staining. FIG. 4 shows the SDS-PAGE separation of cross-linking reaction mixture with molar ratios of RNase S and cross-linker at 1:50 and 1:100. The molecular masses of S-protein, S-peptide, and the cross-link are 11534 Da, 2166 Da, and 908 Da, respectively. The 1:1 cross-linked complex is located at around 14.6 kDa.

As shown in the control lane of FIG. 4, S-protein was detected at expected region while S-peptide was not observed, probably due to the fact it was too small to be retained on the gel. With the cross-linker included in the reaction mixture, a distinctive band above S-protein band was clearly observed on the gel even at the first reaction time point, 15 min, at a reaction ratio of 1:50. The upper bands observed on the gel may be cross-linked complex of S-peptide and S-protein. They appeared at higher molecular weight than 14.6 kDa, likely because the cross-linked complex may migrate slower than expected.

With 100-fold excess of the cross-linker used, all upper bands appeared more intense than lower bands. As compared to a reaction ratio of 1:50, the upper bands in reaction ratio of 1:100 were located at slightly higher position indicating that some dead-end modification or intra-cross-linking of proteins may have occurred. Since 1:1 linkage of interacting proteins is most desirable, reaction ratio of 1:50 at incubation time 15 min was used for the following experiments. For in-gel trypsin digestion, the gel bands were excised carefully to include most proteins with minimum volume. The tryptic digest was further analyzed by nano-LC/MS/MS.

Analysis of Cross-Linked Proteins. The in-gel tryptic digest of cross-linked complex was further analyzed by nano-LC/MS/MS to locate the cross-links. LC/MS/MS data were acquired with the data-dependent mode. As described above, during LC/MS/MS process, detection of ions at m/z 711 indicates the potential existence of the precursor ions carrying cross-links, and observation of ions at. m/z 828 is a signal that precursor ion is a dead-end modified peptide. Therefore, extracted ion chromatograms (EICs) that were built for ions at m/z 711 and 828 and the peaks in EICs provide useful clues for identifying cross-link containing peptide ions. This information can be extremely helpful since it narrows down the search window for cross-links dramatically.

Figure 5:
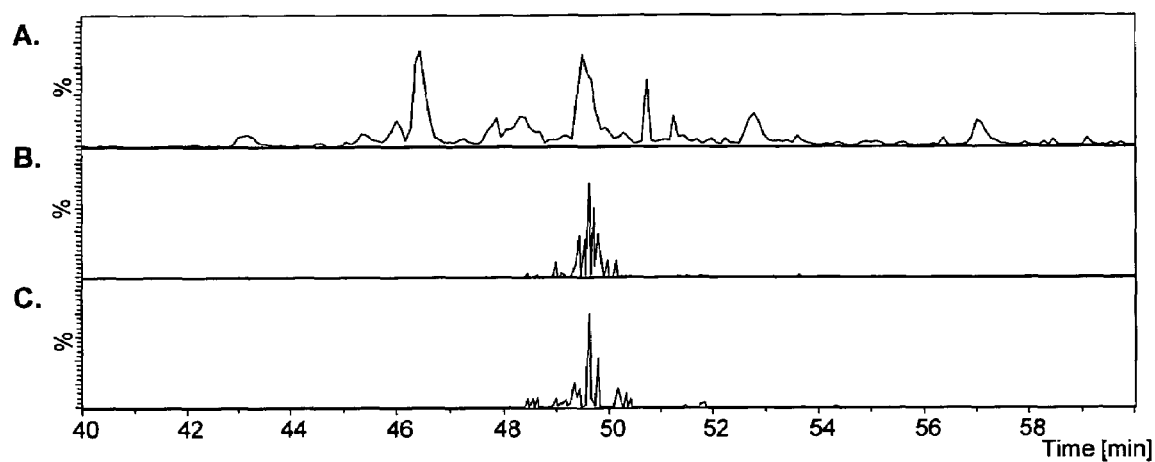
FIG. 5A shows the base peak chromatogram of a Nano-LC/MS/MS analysis of a tryptic digest of cross-linked RNase S complex in accordance with particular inventive aspects. Data was filtered to include MS scan only.
FIG. 5B shows Nano-LC/MS/MS analysis of a tryptic digest of cross-linked RNase S complex, in accordance with particular inventive aspects. This panel shows an EIC of ions at m/z 828.3. Data was filtered to include MS/MS scan only.
FIG. 5C shows a Nano-LC/MS/MS of tryptic digest of cross-linked RNase S complex in accordance with particular inventive aspects. This panel shows an EIC of ions at m/z 711.3. Data was filtered to include only MS/MS scan.

FIGS. 5A-5C present data illustrating the significance of reporter ions for tracking cross-links from a complex tryptic digest mixture. FIG. 5A is the base peak chromatogram which is filtered to have MS scan data only. FIGS. 5B and 5C are the reconstructed EICs for ions at m/z 828 and 711 during MS/MS scans, respectively. The peaks in these EICs indicate that cross-link containing species eluted during retention time 48-51 min.

As guided by these peaks, further analysis focused on these MS/MS spectra which have ions at m/z 828 and 711. Due to the specific cleavage features of the PIR, MS/MS spectra of cross-link containing peptides exhibited relatively simple fragmentation patterns, i.e., most intense peaks are generated from cleavage of labile bonds in the cross-linker.

Figure 6:
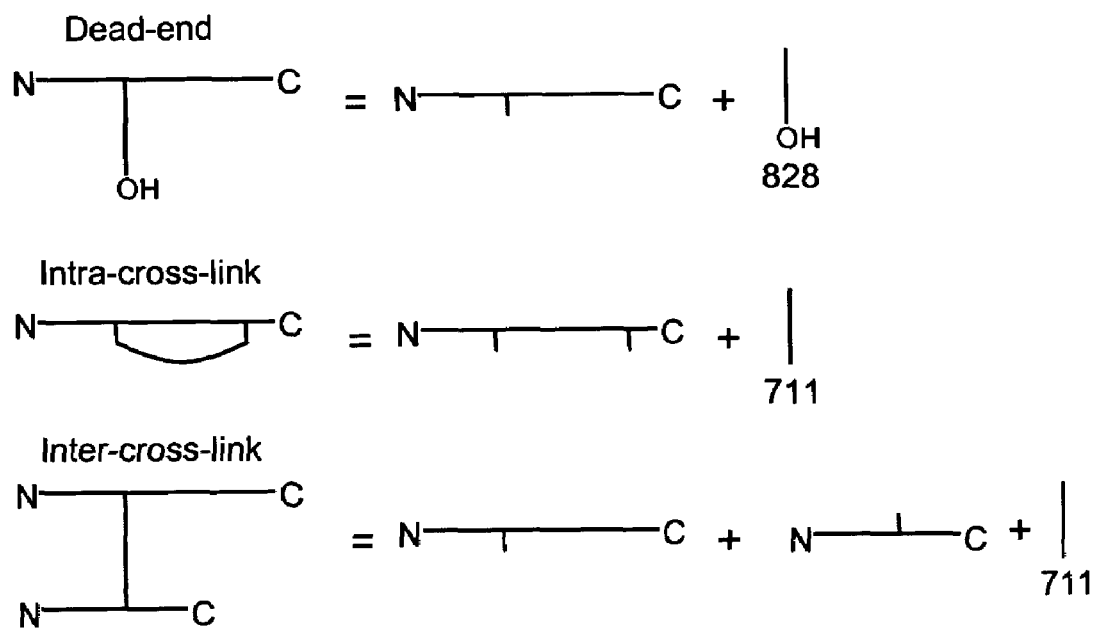
FIG. 6 shows a specific fragmentation pattern that distinguishes, in accordance with particular inventive aspects, between and among dead-end, intra-, and inter-cross-linked peptides.

These simple fragmentation patterns may be further utilized to differentiate dead-end, intra-, or inter-cross-linked peptides as illustrated in FIG. 6. For dead-end modified peptides, the cleavage of the precursor ions generates the reporter ion at m/z 828, and the intact peptide chain with the remaining tag. The m/z of this peptide chain can be deduced by subtracting 828 from the mass of the precursor ion. For cleavage of intra-cross-linked peptides, it was expected that the reporter ions at m/z 711 and ions of the intact peptide chain with two remaining tags would be observed. In this case, the m/z of this peptide chain is the difference of the mass of the precursor ion and 711. If an inter-cross-linked peptide complex is fragmented, two separate intact peptide chains with the remaining tags are generated in addition to reporter ions at m/z 711. Thus, the sum of masses of the two peptide chains should equal the difference of the mass of precursor ion and 711.

Figures 7A, 7B:
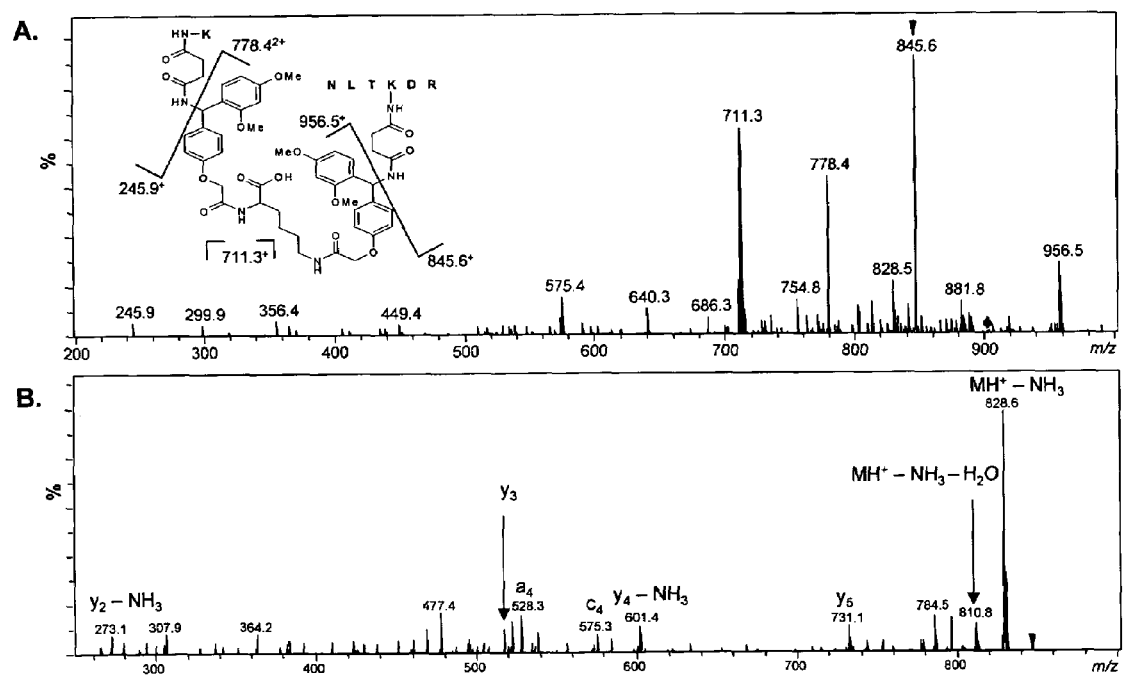
FIG. 7A shows a mass spectrum of inter-cross-linked peptides (K; and NLTKDR (SEQ ID NO:1)) from RNase S complex in accordance with particular inventive aspects. This panel shows MS/MS spectrum of the ions at m/z $900.9^{2+}$ (labeled with a diamond). The structure of the spacer chain in the cross-linker is fully drawn. The most intense peaks were generated from favorable cleavage of labile bonds as indicated in figure.
FIG. 7B shows a mass spectrum of inter-cross-linked peptides from RNase S complex in accordance with particular inventive aspects. This panel shows a $MS^3$ spectrum of ions at m/z 845.6, which is labeled with a triangle.

As directed by the EICs of the reporter ions, an inter-cross-linked peptide was readily identified as shown in FIG. 7. The location of the cross-link was identified to be between tryptic peptide fragment (1-1), Lys 1 of S-peptide and fragment (14-19), NLTKDR (SEQ ID NO:4) of S-protein. The doubly-charged precursor ions at m/z $900.9^{2+}$ were isolated and fragmented. The MS/MS spectrum shows the efficient cleavage of the labile bonds in the spacer chain to generate ions at m/z $245.9^+$, $711.3^+$, $778.4^{2+}$, $778.4^+$, and $845.6^+$ as indicated in FIG. 7A.

By analyzing the MS/MS spectrum, it was further confirmed that the precursor ions were from an inter-cross-linked peptide owing to the fact that the sum of 711, neutral mass 244.9 from one peptide chain, and neutral mass 844.6 from the other peptide chain is equal to the m/z of singly-charged precursor ions. The undisrupted peptide chain at m/z 845.6 was further fragmented by another stage of MS/MS. As shown in FIG. 7B, the fragment ions generated by $MS^3$ supported the assignment of the peptide sequence with the remaining tag attached at Lys 17.

Figure 8:
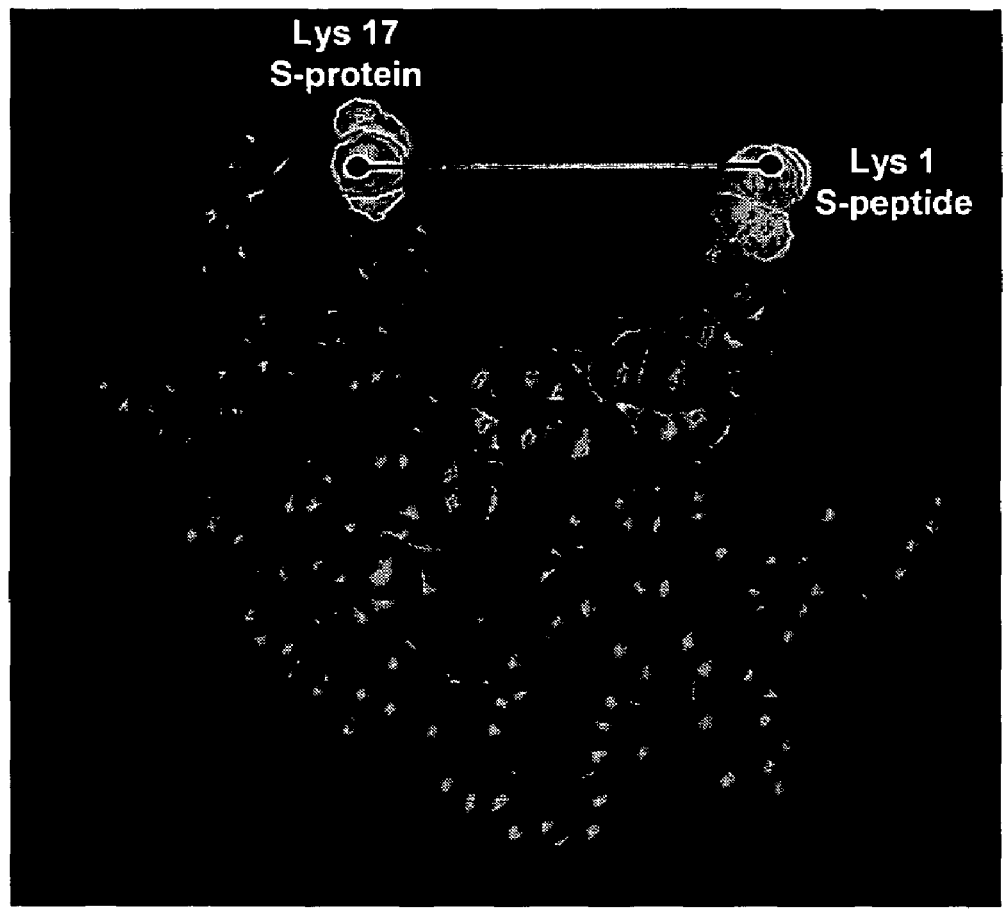
FIG. 8 shows an X-ray structure, and amino acid sequences of RNase S complex in accordance with an embodiment of the present invention. The S-protein domain (SEQ ID NO:3) is marked in blue and the S-peptide domain (SEQ ID NO:2) is marked in pink. The observed cross-linked residues Lys1 of S-peptide and Lys17 of S-protein are underlined in respective sequences, and indicated in yellow in the structure. Cross-link is indicated by the line (red).

FIG. 8 shows the X-ray crystal structure of RNase S and sequences of S-peptide (SEQ ID NO:2) and S-protein (SEQ ID NO:3). Because the peptides were generated by trypsin digestion, the cross-link was assigned to the N-terminal amine instead of the ϵ-amine of Lys 1 in S-peptide since trypsin would likely not cut at this lysine otherwise. The inter-cross-linked peptide from a bigger tryptic peptide fragment (1-7) with one missed cleavage, KETAAAK (SEQ ID NO:6) of S-peptide, was not observed in the mass spectra. This may be because the hydrophobic nature of larger cross-linked peptides makes it difficult to recover them from gels. According to particular aspects, a biotin group can be incorporated in the cross-linker, and affinity purification and other non-gel based separations can thus be employed to purify cross-linked peptides from in-solution enzymatic digest.

No other cross-links were identified except for a dead-end modification that was observed on Lys 17 of S-protein. Without being bound by mechanism, the space-filling model of the RNase S crystal structure shown in FIG. 8 provides insight into why a cross-link was formed between the N-terminus of the S-peptide and Lys 17 of the S-protein. The N-terminus of S-peptide and Lys 17 of S-protein are well exposed to solvent, and thus have good accessibility for cross-linking reaction. This is consistent with reported observation that residues 3-13 of the S-peptide and 96-100 of S-protein are involved in binding (Wyckoff, H. W. et al., *J Biol Chem* 242:3749-3753, 1967; Taylor, H. C. et al., M. *Proc Natl Acad Sci USA* 82:6423-6426, 1985).

In addition, the cross-linking reaction mixture was analyzed directly in the absence of tryptic digestion using nano-LC/MS/MS to check for modifications of S-peptide. An aliquot of cross-linking reaction mixture with a 100-fold excess of cross-linker that had an incubation time of 30 min was precipitated by TCA to remove salts and most of the unreacted cross-linker. The precipitated peptides were resuspended in 10% acetonitrile solution and loaded to the nano-LC column for LC/MS/MS analysis. Both for MS of S-peptide 1-19 and 1-20 were observed to be modified by cross-linking reactions to generate dead-end and intra-cross-linked peptides.

Figures 9A, 9B:
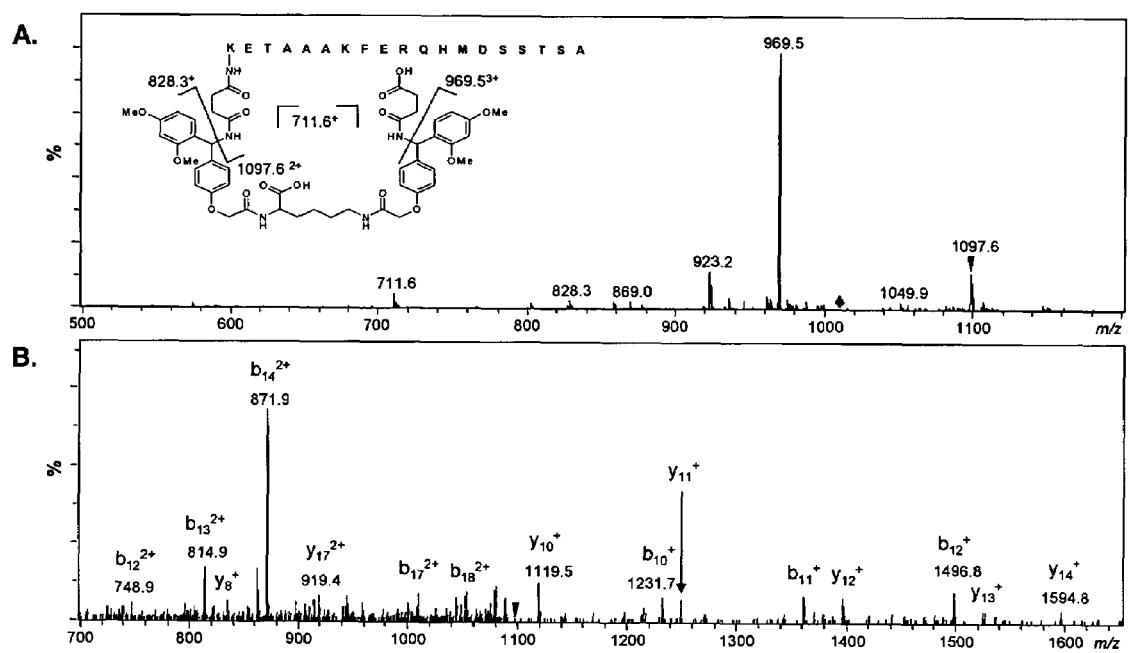
FIG. 9A shows a mass spectrum of a dead-end modified peptide (KETAAAKFERQHMDSSTSA; (SEQ ID NO:4)) from RNase S complex. This panel shows a MS/MS spectrum of the ions at m/z $1007.3^{3+}$, which is labeled with a diamond. The structure of the spacer chain in the cross-linker is fully drawn.
FIG. 9B shows a mass spectrum of a dead-end modified peptide from RNase S complex. This panel shows a $MS^3$ spectrum of ions at m/z $1097.6^{2+}$, which is labeled with a triangle.

FIG. 9 shows exemplary mass spectra of the dead-end modified S-peptide 1-19. The triply-charged precursor ions at m/z 1007.3 were isolated and fragmented by MS/MS. The majority of fragmentation took place at two labile bonds in the spacer chain to generate a simple $MS^2$ spectrum. As shown in FIG. 9A, ions at m/z $711.6^+$, $1097.6^{2+}$, and $969.5^{3+}$ were dominant in the spectrum. The observation of ions at m/z $1097.6^{2+}$ further confirmed that the precursor was a dead-end modified peptide, since they were produced from the precursor ions by losing the reporter ions at m/z 828.

To get sequence information of the intact peptide chain, ions at m/z $1097.6^{2+}$ were isolated for $MS^3$. As shown in FIG. 9B, the observation of a series of b ions ($b_{10}$, $b_{11}$, $b_{12}$, $b_{13}$, $b_{14}$, $b_{17}$, and $b_{18}$) provided the sequencing information for the modified S-peptide. In particular, the existence of fragment ions at $y_{13}$ and $y_{14}$ confirmed that the modification occurred at N-terminus or ε-amine of Lys 1 of S-peptide, but not Lys 7. An intra-cross-linked S-peptide 1-19 was also identified. The precursor ions at m/z $1001.3^{3+}$ were isolated and fragmented by MS/MS.

Figures 10A, 10B:
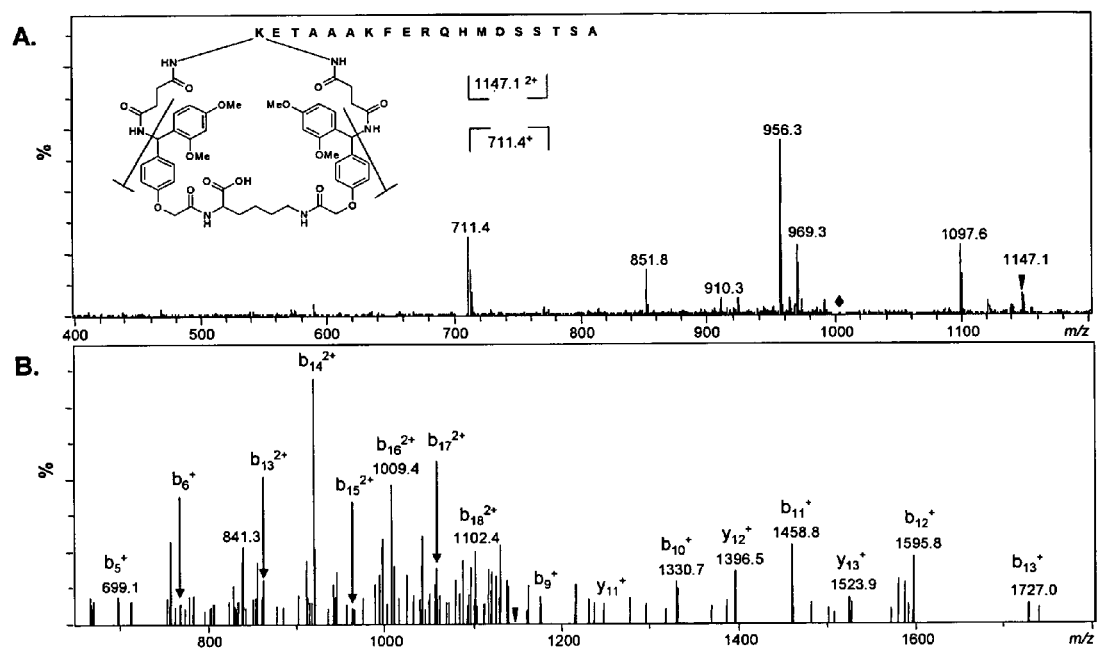
FIG. 10A shows a mass spectrum of an intra-cross-linked peptide (KETAAAKFERQHMDSSTSA; (SEQ ID NO:4)) from RNase S complex. This panel shows a MS/MS spectrum of the ions at m/z $1001.3^{3+}$, which is labeled with a diamond. The structure of the spacer chain in the cross-linker is fully drawn. The most intense peaks were generated from favorable cleavage of labile bonds as indicated in the figure.
FIG. 10B shows a mass spectrum of an intra-cross-linked peptide from RNase S complex. The panel shows a $MS^3$ spectrum of ions at m/z $1147.1^{2+}$, which is labeled with a triangle.

FIGS. 10A and 10B show the fragmentation results. Due to the cleavage of two labile bonds in the spacer chain, ions at m/z $711.4^+$ and $1147.1^{2+}$ were detected, which also gave an indication that the precursor ions were from an intra-cross-linked peptide since the sum of the neutral masses of these two ions equals the neutral mass of the precursor ion. Ions at m/z $956.3^{3+}$ were produced from cleavage of one labile bond in the spacer chain with additional loss of a di-methoxyl phenyl group. Ions at m/z $969.3^{3+}$ were formed by cleaving one labile bond and the remaining tag in the peptide. These ions were further cleaved at the other labile bond to generate ions at m/z $1097.6^{2+}$. The peptide ions at m/z $1147.1^{2+}$ were isolated for further fragmentation by $MS^3$. The fragmentation pattern was observed to be similar among S-peptide 1-19 (KETAAAKFERQHMDSSTSA; (SEQ ID NO:4)) with two tags as shown in FIG. 10B, one tag as shown in FIG. 9B, and S-peptide 1-19 itself, indicating the remaining tags did not interfere the fragmentation of the peptide chain. The fragment ions observed at $b_5$, $b_6$, and $y_{13}$ in FIG. 10B confirmed that the intra-cross-link was formed between α-amine at N-terminus and ε-amine of Lys 1 and Lys 7 in S-peptide was not involved.

The three $MS^2$ and $MS^3$ spectra presented here illustrate that this cross-linking strategy can effectively distinguish dead-end, intra-, and inter-cross-linked peptides. The data also indicates that the bulky spacer chain in the disclosed cross-linker did not affect its cross-linking capability. Nevertheless, the use of the bulky spacer was able to generate a reasonable size of reporter ions to be detected by any type of tandem mass spectrometer. The release of the bulky group not only provided reporter ions, but also made it convenient for efficient fragmentation of peptide chains with short tags during $MS^3$.

Additionally, the maximum UV absorption wavelength of the cross-linker was measured to be 280 nm, which is different than that of most peptides (214 nm). This feature may be used as an additional handle for retrieving peptides carrying inventive cross-links. It is likely that the cross-linker is not rigid in solution, and that the bonds in the cross-linker are flexible and may be folded in different confirmations to give a broad range of distances between the two reactive groups. This feature, or strategic adjustment of this feature, may have utility for general protein-protein interaction studies.

For the inter-cross-link identified between the N-terminus of S-peptide and Lys 17 of S-protein, the distance was estimated to be 14 Å from X-ray structure. In the intra-cross-linked S-peptide 1-19 (SEQ ID NO:4), the cross-link was formed between the α-amine of N-terminus and the ε-amine of Lys 1 instead of Lys 7. The maximum distance of the α-amine of N-terminus and the ε-amine of Lys 1 was calculated to be 9.1 Å. These observations further indicate that the cross-linker is fairly flexible in solution to react with the most accessible primary amines in proximity.

EXAMPLE 2

New Protein Interaction Reporters Having Substantial Utility for, e.g., Profiling Interactome by FTICR Mass Spectrometry were Developed Experimental Methods:

Chemicals. Chemicals were purchased from Sigma-Aldrich (St. Louis, Mo., USA) or Novabiochem (San Diego, Calif., USA) unless otherwise stated. Cross-linking reactions of Sub P (RPKPQQFFGLM) (SEQ ID NO:5) (1 µL, 1 mM) and PIR-1 and PIR-3 were performed in 100 uL PBS buffer at pH 7.2. The molar ratio of Sub P and cross-linker was maintained 1:2. The reactions were conducted for 1 h at room temperature. After 1 h, the reactions were terminated by adding 50 µL of 10 mM tris buffer. The salt was removed from the solution by SepPack™ C18 (Water, Milford, Mass., USA).

All FTICR-MS spectra were obtained with a Bruker Daltonics, 7T APEX Q-FTICR mass spectrometer by direct infusion of samples in a nano ESI source made with a fused capillary (360 µm o.d., and 20 µm i.d) and the capillary tip was etched with 49% HF. The FTICR mass spectra were processed with the software, ICR-2LS, developed by Pacific Northwest National Laboratory (Anderson, G A, Bruce J E, Eds, *ICR-2LS* 1995, Pacific Northwest National Laboratory: Richland, Wash., 1995). The electrospray solution was acetonitrile/0.1% TFA or 50 mM ammonium acetate unless otherwise mentioned.

Electron capture dissociation (ECD) was performed using a heated hollow cathode dispenser located outside the ICR cell to obtain the MS/MS data. The cathode dispenser was heated gradually to 1.8A-1.9A. Side kick trapping voltage was maintained between +6 V to −6 V. Electrons used for ECD were accelerated with 3 V. The electron injection time was 200 ms.

Synthesis of PIRs. The cross-linkers (PIR-1, PIR-2 and PIR-3), as shown in FIGS. 11A-11C, were synthesized using 431A Peptide Synthesizer (Applied Biosystem Foster City, Calif., USA) with solid phase peptide synthesis chemistry. Glycine was coupled to HMPB-MBHA (4-hydroxymethyl-3-methoxyphenoxybutyric acid) resin using the standard symmetric anhydride method.

For PIR-1 and PIR-2, the biotin and PEG group was added in the form of Fmoc-Glu (biotinyl-PEG)-OH by using standard coupling chemistry. The second lysine in the form of Fmoc-lys-ε-Fmoc was coupled to the Fmoc-Glu (biotinyl-PEG)-OH that then formed the branch point for the cross-linkers. The Rink groups, succinic acids, and N-hydroxysuccinamides (NHS) were coupled using same standard activation, coupling and deprotection chemistry.

For PIR-2 one photo-cleavable group, Fmoc-aminoethyl photo linker was introduced in between lysine and Glu(biotinyl-PEG)-OH with the same solid phase chemistry. For PIR-3 which does not contain a biotin group, one alanine residue was coupled with Fmoc-lys-ε-Fmoc to form the branch point of the linkers. The two amino functional groups of the lysine residues are then attached with (3-{[Ethyl-Fmoc-amino]-methyl}-indol-1-yl)-acetic acid. Succinic acids, N-hydroxysuccinamides were coupled as previously described (above). Reduced loading of the resin to about one third is preferred, if not necessary to get efficient coupling of the last step. The final product was cleaved using either 0.5% or 1.0% TFA in chloroform and then neutralized with pyridine. The chloroform and TFA pyridine salt was removed under vacuum until a constant weight was observed.

Formulas, molecular weights and m/e information for PIR-1, -2, and -3 are as follows:

PIR-1
$C_{83}H_{108}N_{12}O_{28}S$
Exact Mass: 1752.7117
Mol. Wt.: 1753.8742
m/e: 1752.7117 (100.0%), 1753.7150 (92.3%), 1754.7184 (42.1%), 1755.7217 (12.6%), 1754.7159 (5.6%), 1755.7193 (5.2%), 1753.7087 (4.5%), 1754.7075 (4.4%), 1754.7121 (4.1%), 1755.7108 (4.1%), 1756.7251 (2.8%), 1756.7226 (2.4%), 1755.7154 (1.9%), 1756.7142 (1.9%), 1753.7179 (1.6%), 1754.7212 (1.5%), 1753.7159 (1.1%), 1754.7192 (1.0%)
C, 56.84; H, 6.21; N, 9.58; O, 25.54; S, 1.83.

PIR-2
$C_{96}H_{124}N_{14}O_{33}S$
Exact Mass: 2032.8176
Mol. Wt.: 2034.1508
m/e: 2033.8210 (100.0%), 2032.8176 (93.7%), 2034.8243 (52.8%), 2035.8277 (18.4%), 2035.8252 (6.6%), 2034.8218 (6.2%), 2034.8180 (5.2%), 2033.8146 (4.9%), 2036.8310 (4.8%), 2035.8168 (4.4%), 2034.8134 (4.1%), 2036.8286 (3.5%), 2035.8213 (2.7%), 2036.8201 (2.3%), 2034.8271 (1.9%), 2033.8238 (1.7%), 2034.8252 (1.3%), 2033.8218 (1.2%), 2037.8319 (1.2%)
C, 56.68; H, 6.14; N, 9.64; O, 25.96; S, 1.58.

PIR-3
$C_{51}H_{61}N_{9}O_{15}$
Exact Mass: 1039.4287
Mol. Wt.: 1040.0813
m/e: 1039.4287 (100.0%), 1040.4321 (56.7%), 1041.4354 (15.8%), 1040.4258 (3.3%), 1041.4330 (3.0%), 1042.4388 (2.9%), 1041.4291 (1.9%), 1042.4363 (1.7%)
C, 58.89; H, 5.91; N, 12.12; O, 23.07.

Figures 12A, 12B, 12C:
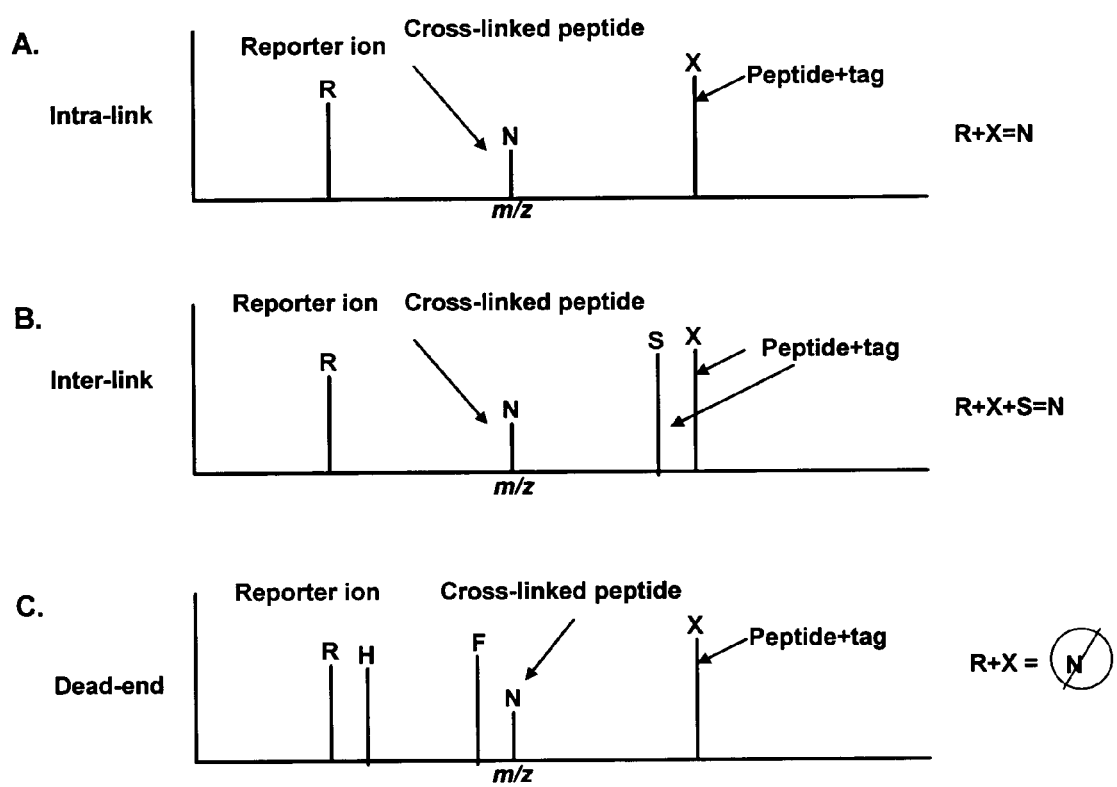
FIG. 12A shows a schematic representation of mass spectral determination of intra cross-linked peptides in accordance with an embodiment of the present invention. If cross-linked peptide is intra-cross-linked, the resulting cross-linked peptide in low energy CID will generate a spectrum similar to the spectrum shown here. The sum of peptide mass with tag should be equal to the observed mass of the cross-linked peptide.
FIG. 12B shows a schematic representation of mass spectral determination of inter-cross-linked peptides in accordance with an embodiment of the present invention. If the peptides are inter-linked, PIR fragmentation will generate two peptide ions and a reporter ion that sum to equal the precursor mass are shown.
FIG. 12C shows a schematic representation of mass spectral determination of 'dead-end' cross-linked peptides in accordance with an embodiment of the present invention. For dead-end labeling, the sum of peptide with tag mass and reporter mass should not equal the cross-linked peptide mass. Two additional marker ions may appear in the spectrum for dead-end cross-linking. One is fragmentation of one labile bond from a coupled end of the cross-linker, which is always constant for a particular hydrolyzed PIR (peak "H"). The other mass may appear from the fragmentation of one labile bond from the hydrolyzed end of the cross-linker. This mass (peak "F") depends on the cross-linked peptide mass and may easily be distinguished by subtracting this mass from the precursor dead-end cross-linked peptide mass (peaks "N"–"F").

Strategy to distinguish dead-end, intra and inter cross-linked peptides. The cross-linkers were designed with two reactive groups and two low energy MS/MS cleavable bonds. PIR-1 and PIR-2 incorporate biotin for sample enrichment. The interacting peptides are identified by looking at the reporter ion loss in the MS spectra which also can distinguish cross-linked and non specific interaction. For an intra-link peptide, the sum of the mass of the reporter ion and peptide mass should match the mass of cross-linked peptide mass (FIG. 12A). If two proteins are cross-linked, the sum of the peptide masses generated in low energy MS/MS and reporter ion mass should sum to match PIR-labeled precursor (FIG. 12B). The dead-end cross-linking products are readily distinguished by adding the peptide mass and reporter ion masses generated by low energy CID experiment. The sum should not match the m/z of PIR labeled dead-end precursor peptide (FIG. 12C). For dead-end cross-linking two additional fragments ion can appear in the spectra. One is fragmentation of one labile bond from a coupled end of the cross-linker, which is always constant for particular hydrolyzed PIR (peak "H"). The other mass can appear from the fragmentation of one labile bond from a hydrolyzed end of the cross-linker. This mass (peak "F") depends on the cross-linked peptide mass and is readily distinguished by subtracting this mass from the precursor dead-end cross-linked peptide mass (peaks "N"-"F").

Results:

An additional feature of protein interaction reporter-1 (PIR-1) is incorporation of a hydrophilic side chain in the cross-linker (FIG. 11A). Most of the current commercial cross-linkers are hydrophobic in nature. This makes a very difficult task to react proteins in their physiological pH 7. To make this cross-linker less hydrophobic a polyethylene glycol chain residue was incorporated in the cross-linker to improve solubility in aqueous buffer. In addition, a biotin moiety was introduced to allow enrichment of cross-linked peptides from complex mixtures.

Figures 13A, 13B, 13C, 13D:
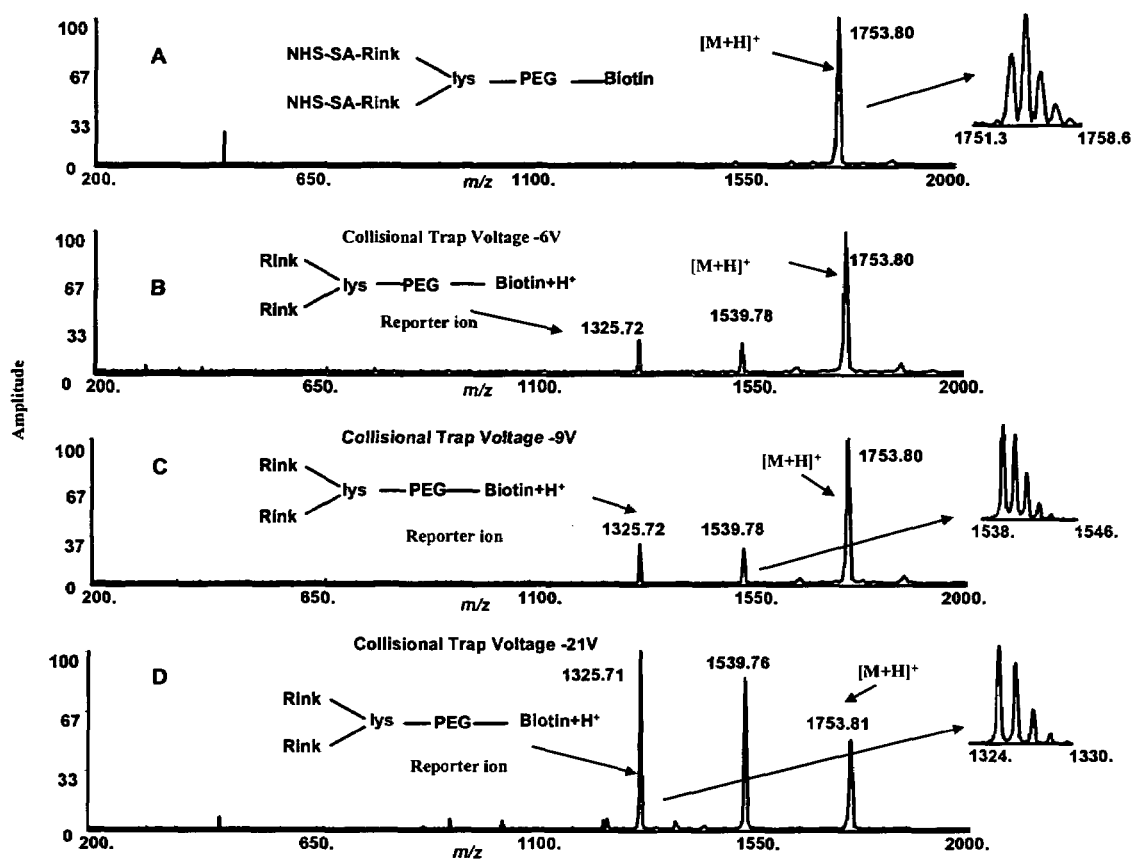
FIG. 13A shows a gas phase fragmentation of PIR-1 in ESI-FTICR-MS. Electro spray solution was acetonitrile/0.1% TFA. The isolated m/z corresponds to molecular weight of PIR-1 subjected to different collisional trap voltages. Mass spectra are shown for −3 V.
FIG. 13B shows a gas phase fragmentation of PIR-1 in ESI-FTICR-MS. Electro spray solution was acetonitrile/0.1% TFA. The isolated m/z corresponds to molecular weight of PIR-1 subjected to different collisional trap voltages. Mass spectra are shown for −6 V. The distinctive reporter ion was observed at m/z 1325.71, following the cleavage of both low energy mass spectrometry labile bonds. The peak at m/z 1539.76 corresponds to cleavage of one mass spectrometry labile bond.
FIG. 13C shows a gas phase fragmentation of PIR-1 in ESI-FTICR-MS. Electro spray solution was acetonitrile/0.1% TFA. The isolated m/z corresponds to molecular weight of PIR-1 subjected to different collisional trap voltages. Mass spectra are shown for −9V. The distinctive reporter ion was observed at m/z 1325.71, following the cleavage of both low energy mass spectrometry labile bonds. The peak at m/z 1539.76 corresponds to cleavage of one mass spectrometry labile bond.
FIG. 13D shows a gas phase fragmentation of PIR-1 in ESI-FTICR-MS. Electro spray solution was acetonitrile/0.1% TFA. The isolated m/z corresponds to molecular weight of PIR-1 subjected to different collisional trap voltages. Mass spectra are shown for −21V. The distinctive reporter ion was observed at m/z 1325.71, following the cleavage of both low energy mass spectrometry labile bonds. The peak at m/z 1539.76 corresponds to cleavage of one mass spectrometry labile bond.

For studies of the gas phase fragmentation behavior of this cross-linker, protein interaction reporter 1 (PIR-1) was dissolved in acetonitrile/0.1% TFA. Water was avoided in the spray solution to prevent the hydrolysis of the reactive groups. A 10 μM solution was directly infused with a nano-electrospray source using flow rate of 20 μL/min. m/z (1753.80 Da), corresponds to the +1 charge state of calculated molecular weight of the PIR-1 (FIG. 13). The ions at m/z 1753.80 were isolated with a quadrupole and accumulated hexapole at −3 V collisional trap cell voltage (FIG. 13A). To activate the PIR, the collisional trap voltage was increased at three volt increments to fragment labile bonds (FIGS. 13B-13D). The characteristic cleavage of two low energy MS/MS cleavable bonds was evident from the mass spectra. Two fragment ions appeared in the spectra, m/z 1539.78 and m/z 1325.72, which correspond to the fragmentation of two MS/MS cleavable bonds (1753.80−1539.78=214.02 Da, 1539.78−1325.72=214.06 Da, expected 214.05 Da).

The expected reporter ion m/z 1325.72 (+1), appeared in the MS spectra after fragmentation of two MS/MS cleavable bonds. After the cross-linking application, the m/z 1539.78, which corresponds to the cleavage of one MS/MS cleavable bond, should not appear in the mass spectrum at same m/z if coupled with a peptide. The m/z 1325.72, which corresponds to the cleavage of two MS/MS cleavable bonds, should always appear at the mass spectra at the same m/z after cross-linking, and was designated as reporter ion.

The increase of collisional trap voltage (−6 V, −9 V, −21 V) increased the intensity of one bond cleavage and reporter fragment ion intensity (FIGS. 13B-13D). These spectra showed the efficiency of release of reporter ion from cross-linker alone and demonstrated the potential of this PIR-1 to release specific reporter ions. Generally, peptides fragment with collisional cell voltage of −18 V to −27 V, depending on charge states. These data showed that with these acceleration voltages (−6 V, −9V, −21V), the cross-linker backbone remained intact while efficient fragmentation on the low energy MS/MS cleavable bonds was observed.

To enrich sample of cross-linked peptides, a biotin group was introduced in the PIR cross linkers. To remove the biotin tag following an enrichment step, a photo-cleavable group was introduced into PIR-2 for more efficient sample recovery (FIG. 11B). This photo-cleavable group may be cleaved by exposure to UV light at around 360 nm (Zhou, H. et al., Nat Biotechnol 20:512-515, 2002; incorporated by reference herein).

Figures 14A, 14B, 14C, 14D:
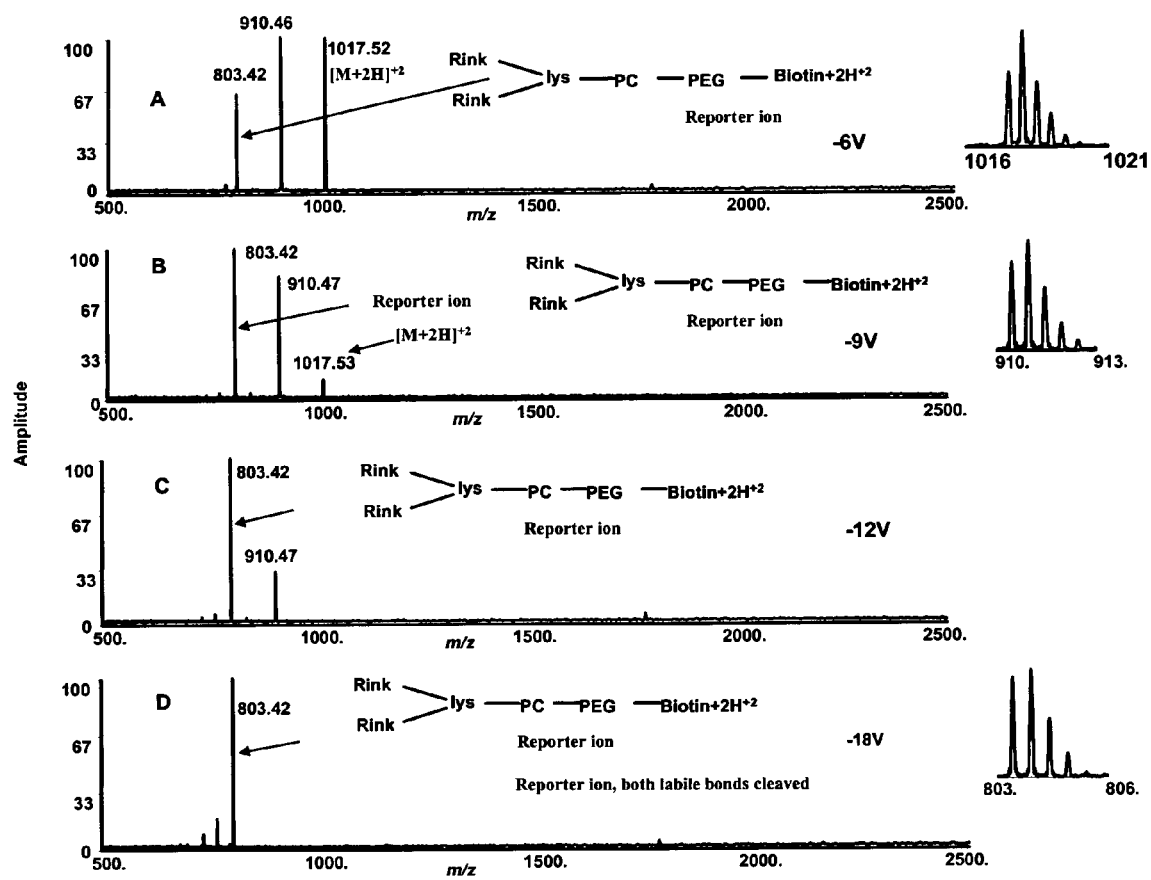
FIG. 14A shows a gas phase fragmentation of PIR-2 in ESI-FTICR-MS in accordance with an embodiment of the present invention. The electrospray solution was acetonitrile/0.1% TFA. A photo-cleavable group was introduced in the linker to allow efficient sample recovery. The isolated m/z corresponds to the molecular weight of PIR-2, m/z 1017.52 (+2 charge state) subjected to different collisional trap voltages. A mass −6 V spectrum is shown here. Distinctive reporter ion was observed at m/z 803.42 (1017.52−803.42=m/z 214.1 Da) following the cleavage of both low energy mass spectrometry labile bonds. The photo-cleavable bond remained intact during low energy MS/MS experiment. The m/z 910.47 corresponds to cleavage of one mass spectrometry labile bonds (m/z 1017.52−910.47=m/z 107.05 Da).
FIG. 14B shows a gas phase fragmentation of PIR-2 in ESI-FTICR-MS in accordance with an embodiment of the present invention. Electrospray solution was acetonitrile/0.1% TFA. A photo-cleavable group was introduced in the linker to allow efficient sample recovery. The isolated m/z corresponds to the molecular weight of PIR-2, m/z 1017.52 (+2 charge state) subjected to different collisional trap voltages. A −9V mass spectrum is shown here. Distinctive reporter ion was observed at m/z 803.42 (1017.52−803.42=m/z 214.1 Da) following the cleavage of both low energy mass spectrometry labile bonds. The photo-cleavable bond remained intact during low energy MS/MS experiment. The m/z 910.47 corresponds to cleavage of one mass spectrometry labile bonds (m/z 1017.52−910.47=m/z 107.05 Da).
FIG. 14C shows a gas phase fragmentation of PIR-2 in ESI-FTICR-MS in accordance with an embodiment of the present invention. Electrospray solution was acetonitrile/0.1% TFA. A photo-cleavable group was introduced in the linker to allow efficient sample recovery. The isolated m/z corresponds to the molecular weight of PIR-2, m/z 1017.52 (+2 charge state) subjected to different collisional trap voltages. A −12 V mass spectrum is shown here. Distinctive reporter ion was observed at m/z 803.42 (1017.52−803.42=m/z 214.1 Da) following the cleavage of both low energy mass spectrometry labile bonds. The photocleavable bond remained intact during low energy MS/MS experiment. The m/z 910.47 corresponds to cleavage of one mass spectrometry labile bonds (m/z 1017.52−910.47=m/z 107.05 Da).
FIG. 14D shows a gas phase fragmentation of PIR-2 in ESI-FTICR-MS in accordance with an embodiment of the present invention. Electrospray solution was acetonitrile/0.1% TFA. A photo-cleavable group was introduced in the linker to allow efficient sample recovery. The isolated m/z corresponds to the molecular weight of PIR-2, m/z 1017.52 (+2 charge state) subjected to different collisional trap voltages. A −18 V mass spectrum is shown here. Distinctive reporter ion was observed at m/z 803.42 (1017.52−803.42=m/z 214.1 Da) following the cleavage of both low energy mass spectrometry labile bonds. The photocleavable bond remained intact during low energy MS/MS experiment. The m/z 910.47 corresponds to cleavage of one mass spectrometry labile bonds (m/z 1017.52−910.47=m/z 107.05 Da).

To determine if the photo-cleavable group had any effect on release of reporter ions from cross-linkers, the gas phase fragmentation of this linker was studied with FTICR-MS. The cross-linker was directly infused into the nano-electrospray source as previously described for PIR-1. This cross-linker is larger in size due to the PEG and photo-cleavable groups. In this case, the m/z 1017.52 corresponds to the intact +2 charge state of PIR-2 (FIG. 14A). These ions were isolated in quadrupole and fragmented in a collisional trap with different voltage settings.

The fragmentation showed at −6 V, −9V, −12 V and −18 V effective collision energies (FIGS. 14A-14D). The fragmentation of one (1017.52−910.46=107.06*2=214.12 Da) and two (910.46−803.42=107.04*2=214.08 Da) labile bonds were observed. The complete fragmentation of molecular ion m/z 1017.52 to generate only the reporter ion (m/z 803.42 Da) in the mass spectrum was observed at −18 V (FIG. 14D).

In both cross-linkers PIR-1 and PIR-2, a Rink group was used to incorporate low energy MS/MS cleavable bonds. The Rink group has acid cleavable properties and is found to fragment under low energy CAD conditions in the gas phase (Rink, H.; Tetrahedron Lett. 28:3787-3790, 1987; Tang, X. et al., Anal Chem 77:311-318, 2005). In additional aspects, other acid cleavable groups can show similar low energy fragmentation features in FTICR-MS and thus have utility. For example, an additional exemplary cross-linker was designed and synthesized, and comprises an indole acetic acid group in the place of Rink groups was (FIG. 11C). For PIR development this seemed promising since the acid labile properties and synthesis of ethyl amide with (3-{[Ethyl-Fmoc-amino]-methyl}-indol-1-yl)-acetic acid was reported (Estep, K. G. et al., J. Org. Chem 63:5300-5301, 1998). While the Rink group cleavage was observed with 95% TFA, this group can be cleaved with much more mild acid conditions of 5% TFA. For these investigations, the cross-linker was dissolved in acetonitrile/0.1% TFA and the nano-electrospray was used as previously described for PIR-1 and PIR-2. m/z 1040.4 corresponds to the molecular weight of intact cross-linker and this ion was isolated in quadrupole.

Figures 15A, 15B, 15C:
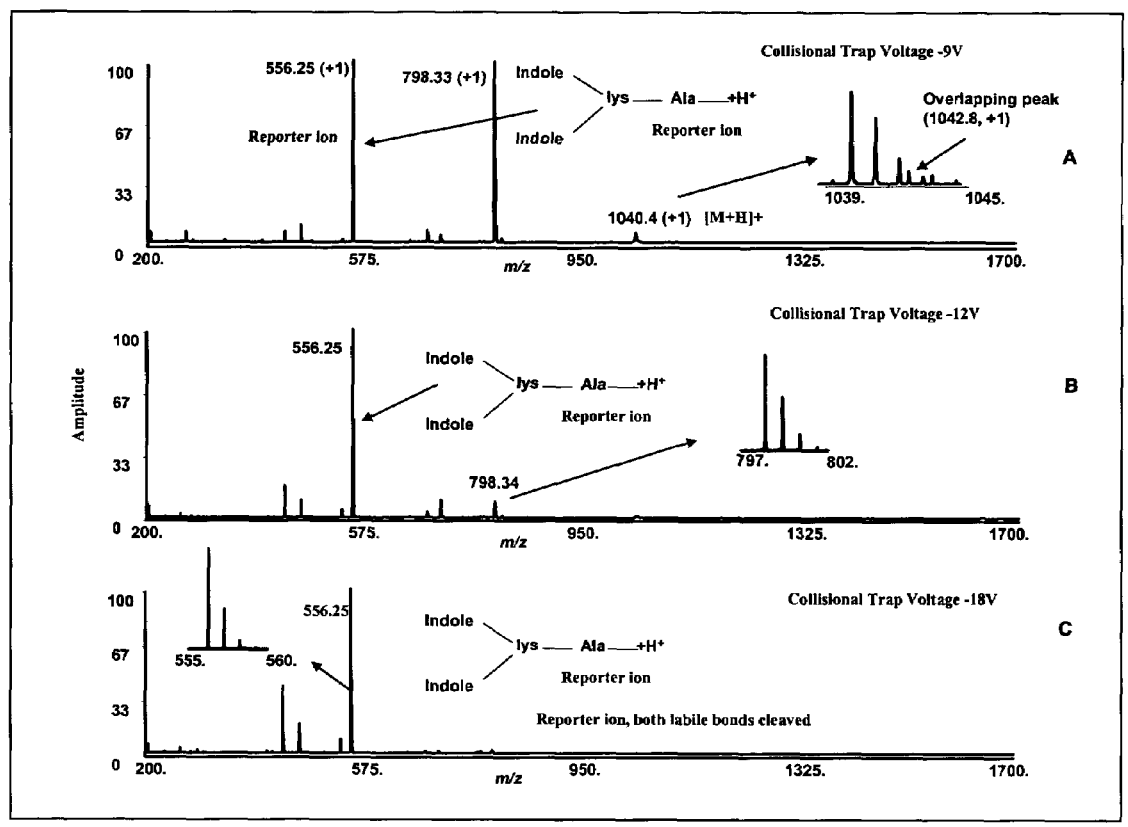
FIG. 15A shows a gas phase fragmentation of PIR-3 in ESI-FTICR-MS in accordance with an embodiment of the present invention. The isolated m/z peak corresponds to molecular weight of PIR-3, m/z 1040.4 (+1 charge state) and was subjected to different collisional trap voltages. The mass spectrum shown in this panel was acquired for a collisional cell voltage of −9V. Distinctive reporter ions were observed at m/z 556.25, resulting from the cleavage of both low energy mass spectrometry labile bonds (m/z 1040.4−798.33=m/z 242.07 Da, m/z 798.34−556.25=m/z 242.08), and indicating that the new acid labile indole acetic acid groups efficiently fragmented in low energy CID experiment in FTICR-MS.
FIG. 15B shows a gas phase fragmentation of PIR-3 in ESI-FTICR-MS in accordance with an embodiment of the present invention. The isolated m/z peak corresponds to molecular weight of PIR-3, m/z 1040.4 (+1 charge state) and was subjected to different collisional trap voltages. The mass spectrum shown in this panel was acquired for a collisional cell voltage of −12 V. Distinctive reporter ions were observed at m/z 556.25, resulting from the cleavage of both low energy mass spectrometry labile bonds (m/z 1040.4−798.33=m/z 242.07 Da, m/z 798.34−556.25=m/z 242.08), and indicating that the new acid labile indole acetic acid groups efficiently fragmented in low energy CID experiment in FTICR-MS.
FIG. 15C shows a gas phase fragmentation of PIR-3 in ESI-FTICR-MS in accordance with an embodiment of the present invention. The isolated m/z peak corresponds to molecular weight of PIR-3, m/z 1040.4 (+1 charge state) and was subjected to different collisional trap voltages. The mass spectrum shown in this panel was acquired for a collisional cell voltage of −18 V. Distinctive reporter ions were observed at m/z 556.25, resulting from the cleavage of both low energy mass spectrometry labile bonds (m/z 1040.4−798.33=m/z 242.07 Da, m/z 798.34−556.25=m/z 242.08), and indicated that the new acid labile indole acetic acid groups efficiently fragmented in low energy CID experiment in FTICR-MS.

After isolation of PIR-3, the voltage settings in the hexapole collisional trap were increased as previously described (FIGS. 15A-15C). The compounds showed fragmentation as expected. The both low energy labile bonds (m/z=1040.4−798.33=242.07 Da, m/z=798.32−556.25=242.08 Da) were cleaved. The compound showed efficient release of reporter ions even at −9V collisional trap voltage (FIG. 15C). Both low energy labile bonds fragmented to generate only reporter ion (m/z 556.25) in the mass spectrum was observed at −18 V (FIG. 15C).

All of the protein interaction reporters showed specific fragmentation in gas phase to release the reporter ions. The cross-linking strategy described previously, showed that sum of the m/z reporter ion fragment and original peptide mass with tags will match the molecular weight of the cross-linked peptides (FIGS. 12A-12C). If cross-linked peptides coupled with one end of the reactive group and other end hydrolyzed the mass of the reporter ion and original peptides with tag mass will never match (FIG. 12C). False positive results which are generated by intra, dead and inter-cross-linked peptides may therefore be distinguished.

Figures 16A, 16B, 16C:
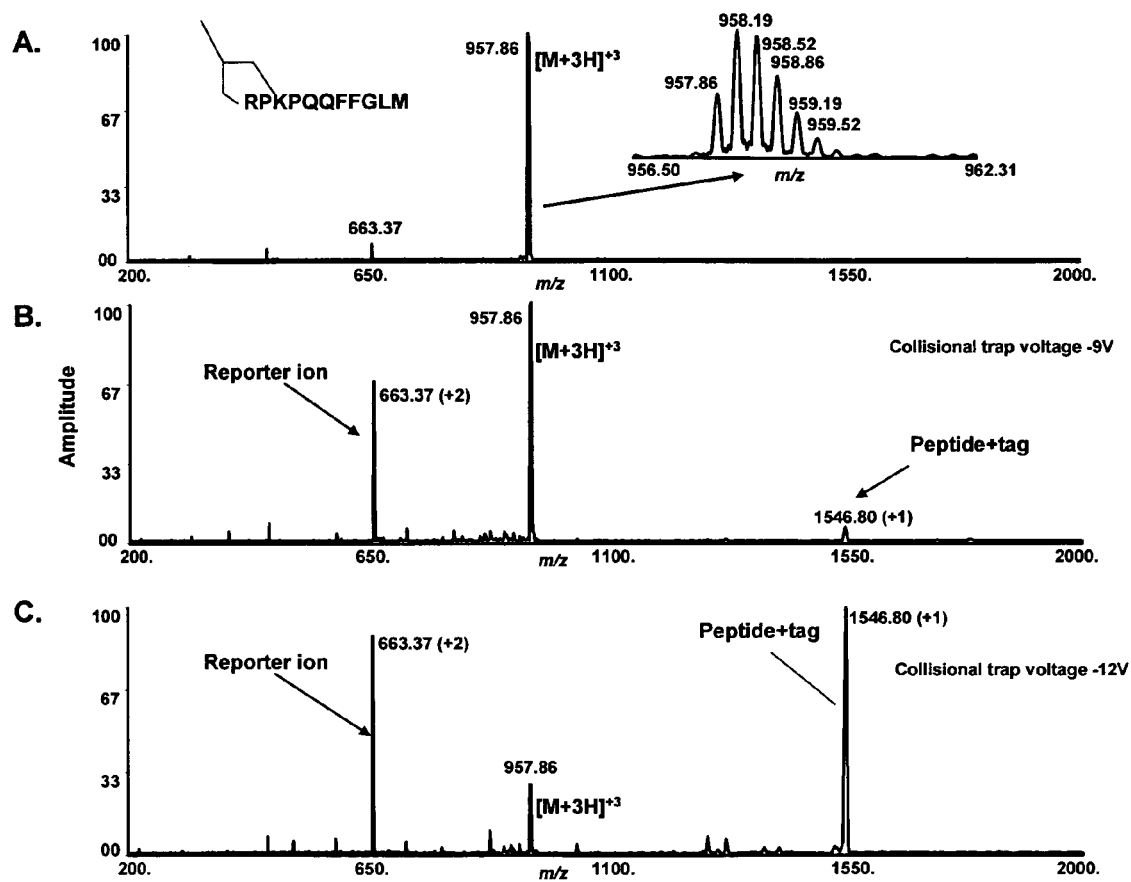
FIG. 16A shows an example of an intra-link Sub P (RPKPQQFFGLM; SEQ ID NO:5) with PIR-1. The peak at m/z 957.86 corresponds to intra-link Sub P and was isolated in quadrupole (1347.71−2H+1752.7117−114.0191−114.0191=2873.39=957.79 (+3 charge state).
FIG. 16B shows an example of an intra-link Sub P with PIR-1. After increasing the collisional trap voltage, the reporter ion (m/z 663.37 Da, +2 charge state) and peptide with two tag masses appeared in the spectra (1347.71+100.0399+100.0399−2H=1545.78 Da) at m/z=1546.80. The expected peptide and reporter masses appeared in the spectra at low collisional cell voltage of −9V. The intensity of peptide and reporter ions was increased with increasing collisional cell voltage.
FIG. 16C shows an example of an intra-link Sub P with PIR-1. The expected peptide and reporter masses appeared in the spectra at low collisional cell voltage of 12 V. The intensity of peptide and reporter ions was increased with increasing collisional cell voltage. No significant fragmentation occurs in peptide and cross-linker backbone other that than the expected low energy cleavable bond.

To demonstrate the utility of these cross-linkers Sub P (RPKPQQFFGLM) (SEQ ID NO:5) was coupled with PIR-1 and PIR-3. Sub P is an 11 mer peptide with molecular weight of 1347.71. The sequence contains two primary amine functional groups. One is on the lysine side chain and other is on the N-terminus. Compounds PIR-1 and PIR-3 were reacted with 1:2 molar ratio with Sub P at pH 7.2. Different molar ratios of cross-linker from 1:2 to 1:10 to 1:25 ratios were tried in the labeling step. It appeared at low 1:2 ratio highest incorporation of cross-linking (~50%) was achieved. After purification of the sample from the salts, the dried solution was reconstituted in 50 mM ammonium acetate. The solution was directly infused in FTICR-MS with conditions as previously described above. m/z 957.86 corresponds to the +3 charge state of intra cross-linked peptides with Sub P (RPKPQQFF-GLM) (SEQ ID NO:5) were isolated in quadrupole and fragmented in the hexapole collisional trap (FIGS. 16A-16C).

The voltage in hexapole collisional trap was first increased to −9V. It is clear from the spectra that two end of the Sub P was intra linked with PIR-1. Two distinctive fragment ions (m/z 1546.80 and m/z 663.37 were observed in the mass spectrum (FIG. 16b). The m/z 1546.80 corresponds to the expected molecular weight if Sub P is intra-linked with PIR (1347.71+100.0399+100.0399−2H=1545.78 Da) and fragmented at both low energy MS/MS cleavable bonds. The efficient release of reporter ion m/z 663.37 with +2 charge state was observed. The intensity of the reporter ions and peptide with tag masses was observed to increase with increased collisional trap voltages (FIG. 16C). +3 ions at m/z 957.86 of intra-linked Sub P match with Sub P and reporter ion masses (m/z 1546.80+663.37*2=m/z 957.84 Da, +3 charge state).

To demonstrate use of this application to distinguish between intra and dead-end linker, the cross-linking reaction of Sub P with PIR-3, which has indole groups substituted for Rink groups (FIG. 17), was further investigated. The calculated m/z for two reactive groups coupled to Sub P was predicted to be 1345.71+1040.42−114.01−114.01=m/z 2158.11. A mass of m/z 2176.71 was observed in the Maldi-TOF mass spectrum. It is possible that a methionine residue in the Sub P became oxidized (+16 Da), or one end of the reactive group was hydrolyzed (+17 Da) while the other end remained coupled to peptides. The m/z 1088.55 Da (+2) was isolated in quadrupole and fragmented with increasing voltage (FIGS. 17A-17C).

Figures 17A, 17B, 17C:
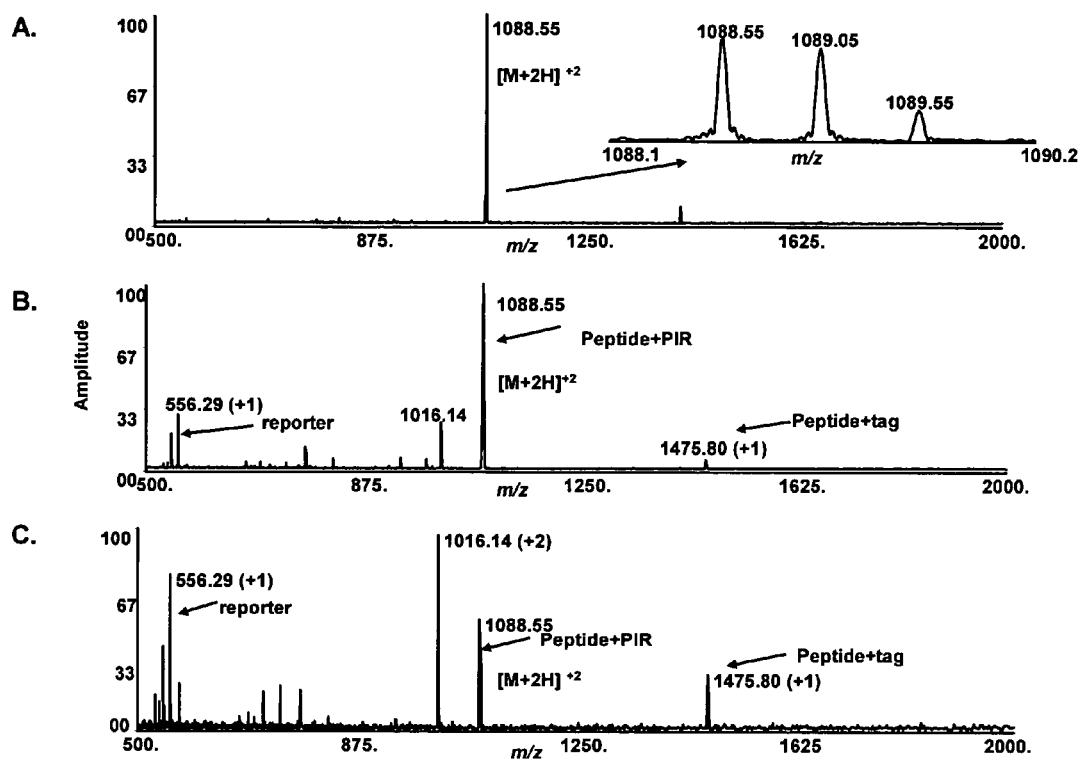
FIG. 17A shows an example of a dead-end cross-linked product of reaction of PIR-3 with Sub P. The peak at m/z 1088.55 corresponds to cross-linked peptides (1347.71−2H+1039.4287−114.0191−114.0191=2157.10 Da), spaced 18 Da apart.
FIG. 17B shows an example of a dead-end cross-linked product of reaction of PIR-3 with Sub P. These ions were isolated and fragmented in hexapole with a collisional cell voltage of −18 V, resulting in the appearance of Sub P with one tag mass (m/z 1475.80) and the reporter ion at m/z 556.29 Da. As expected, in this case, the sum of the peptide mass with tag and reporter mass did not match cross-linked or precursor mass.
FIG. 17C shows an example of a dead-end cross-linked product of reaction of PIR-3 with Sub P. These ions were isolated and fragmented in hexapole with increasing a collisional cell voltage of −27V, resulting in appearance of Sub P with one tag mass (m/z 1475.80) and the reporter ion at m/z 556.29 Da. As expected, in this case the sum of the peptide mass with tag and reporter mass did not match cross-linked or precursor mass. Moreover, m/z 1016.14 Da, as predicted in FIG. 11C appeared from the loss of one low energy labile bond from the hydrolyzed end of (expected 145.07 Da, observed 144.88 Da) the cross-linker. From these data, it is clear from the spectra that Sub P was labeled with a dead-end cross-linking reaction product.

At a −18 V collisional trap voltage, both reporter ion (m/z 556.25 Da) and original Sub P with one tag mass (expected, 1347.71−H+128.07=1475.78 Da) m/z 1475.80 appeared in the spectrum (FIG. 17B). The reporter ions (m/z 556.25 Da) and ions of peptide with tag mass (m/z 1475.80 Da) were observed to increase with increased voltage (−27V) in the collisional trap. These data showed that the cross-linker was coupled in one end of Sub P via a reactive group and other end was hydrolyzed. According to the analysis shown in FIG. 17C, two additional peaks may appear in the spectrum for dead-end cross-linked species. One peak corresponds to fragmentation of one labile bond from the hydrolyzed end of the cross-linker, which will be the loss of 145.07 Da from the dead-end precursor. The other corresponds to fragmentation of another labile bond from the coupled peptide end of the cross-linker. This m/z will be constant irrespective of dead-end precursor m/z. For PIR-3 the dead end hydrolyzed marker ion for the second possibility is m/z 703.52. No hydrolyzed marker ion at m/z 703.52 was observed in the mass spectra, but the fragment ion peak at m/z 1016.16 Da (+2) (corresponding to the loss of one low energy labile bond (144.82 Da)) was observed in the hydrolyzed end of the PIR-3 (FIGS. 17B and 17C). In addition, the sum of the generated reporter and peptide with tag mass did not match the molecular weight of the precursor peptide. This spectrum indicates that the inventive cross-linking strategy distinguishes dead-end cross-linking from other cross-linking species.

Figure 18:
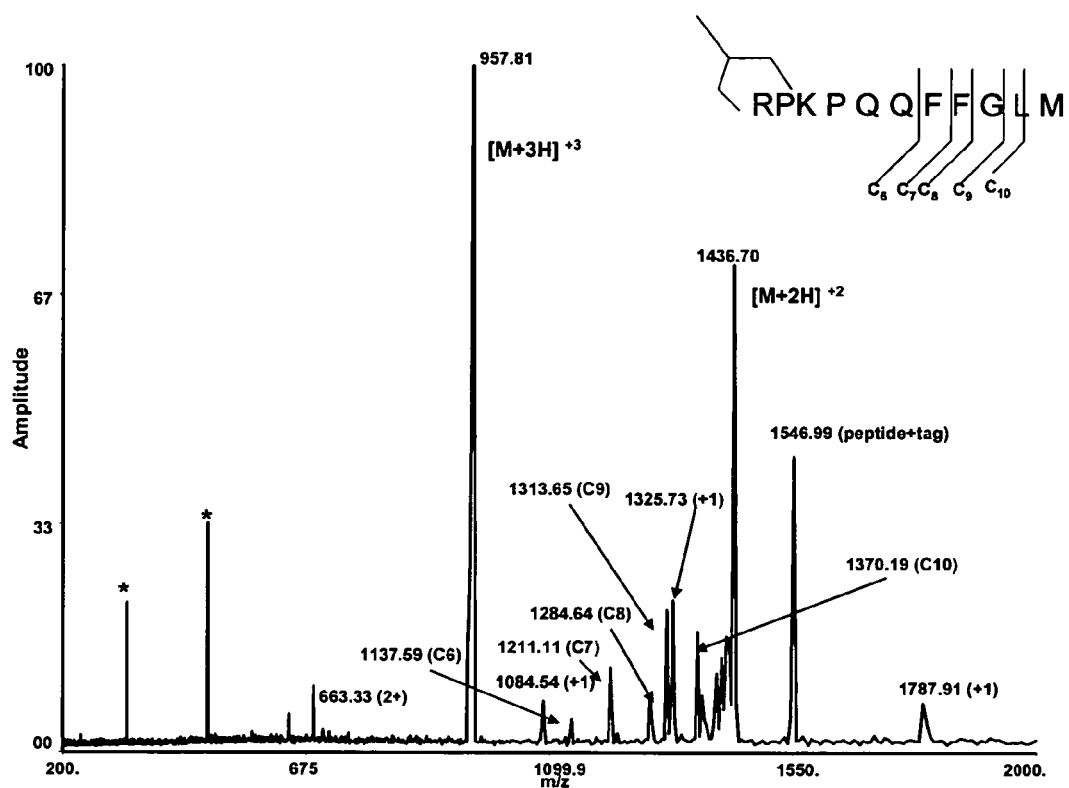
FIG. 18 shows an ECD spectrum of an intra cross-linked peptide with Sub P (RPKPQQFFGLM; SEQ ID NO:5) and PIR-1 (see FIG. 16). The different fragmentation characteristics are obvious from the spectrum. C-type fragment ions from Sub P were generated. All C ions were generated at +2 charge state. A small intensity reporter ion (m/z 663.37) was observed, but peptide with tag masses was observed at high intensity (m/z 1546.99 Da). The cross-linker and peptide were connected with two amide bonds. According to ECD fragmentation characteristics, these two amide bonds cleaved and generated peptide with tag masses with high intensity. From the ions corresponding to peak C (generated by ECD), it can be concluded that this amine reactive cross-linker was intra looped at the N-terminal end of Sub P, where two possible amine functionalities are present, N-terminus and Lysine side chain (* denotes noise peaks).

To sequence the cross-linked peptide, an $MS^3$ can be performed in the peptide and tag mass. The data presented here show that ECD spectrum of the intra-linked Sub P and PIR-1 and their low energy CID are distinctive and can be used to identify PIR labeled cross-linked peptides (FIG. 18). ECD generally cleaves many more backbones sites than collisional activation and keeps labile modifications intact, resulting in complete coverage of a peptide sequence (Zubarev, R. A. et al., *Anal. Chem.* 72:563-573, 2000). From the peak C ions generated by ECD experiment, it can be concluded that Sub P was intra linked at N-terminus and lysine side chain with PIR-1.

These Examples are included for purposes of illustration only, and are not intended to limit the scope of the presently claimed inventive compounds, compositions and methods.

What is claimed is:

1. A protein interaction reporter compound having the Formula I:

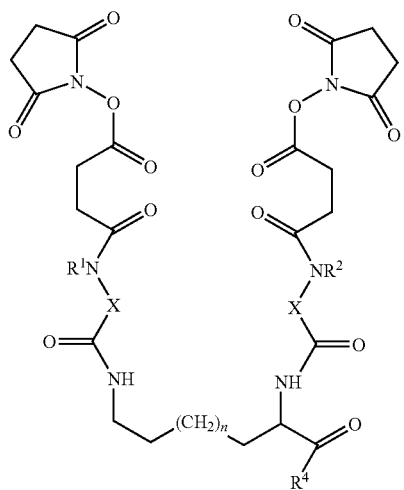

wherein: $R^1$ and $R^2$ are independently H, $CH_3$, or $CH_2$—$CH_3$; n=1-6;

wherein $R^4$ is hydroxyl, or

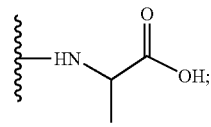

and wherein X is selected from the following:

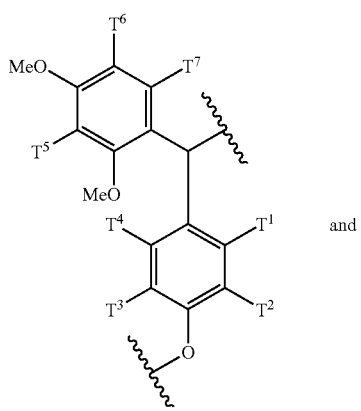

and

-continued

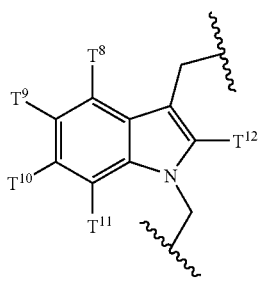

wherein T¹-T¹² are independently hydrogen, $(C_1-C_4)$-alkyl, or $(C_1-C_4)$-alkoxy.

2. The compound of claim 1, wherein X is:

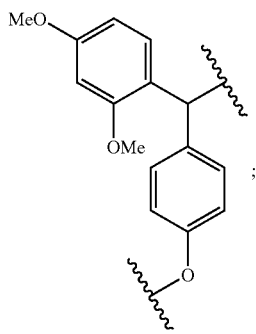

and wherein $R^4$ is hydroxyl.

3. The compound of claim 1, wherein X is:

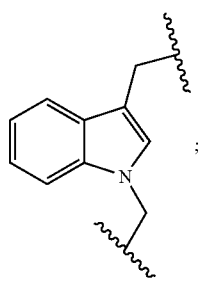

and wherein $R^4$ is

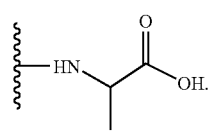

4. A protein interaction reporter compound having the Formula II:

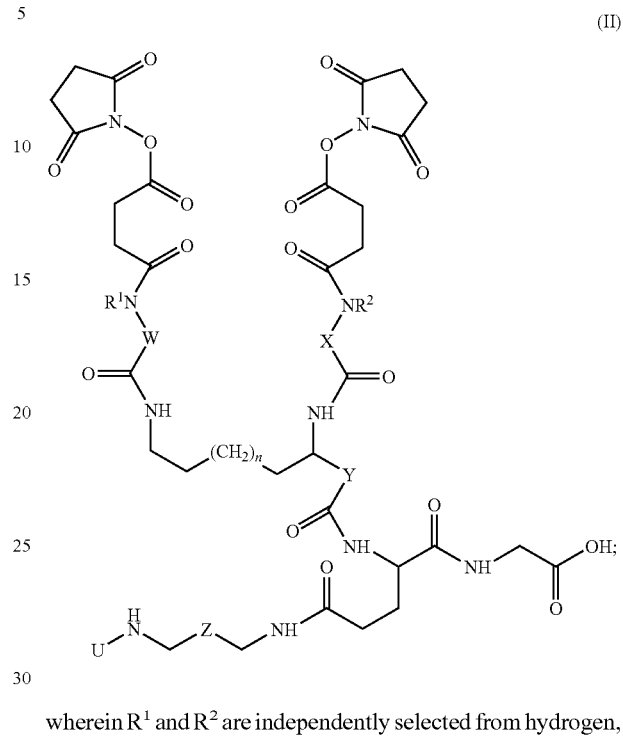

(II)

wherein $R^1$ and $R^2$ are independently selected from hydrogen, or $(C_1-C_4)$-alkyl;

wherein: n=1-6; and W and X are independently selected from:

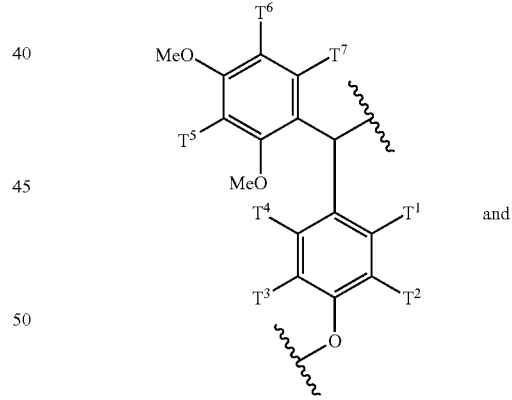

and

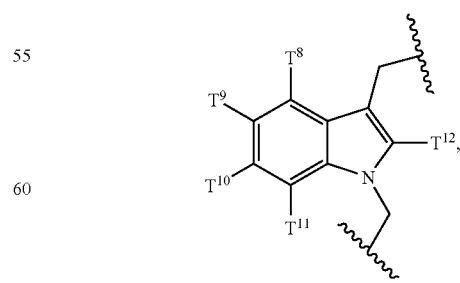

wherein T¹-T¹² are independently hydrogen, $(C_1-C_4)$-alkyl, or $(C_1-C_4)$-alkoxy;

wherein Y is nothing or

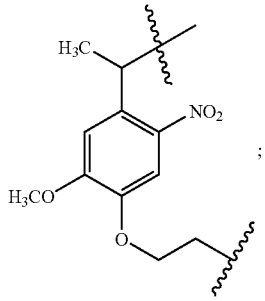

wherein Z is: (—CH$_2$—CH$_2$—O—)$_m$; (—CH$_2$—)$_q$; (—CO—CH$_2$—)$_r$; (—CH$_2$—CO$_2$—)$_r$; (—CH$_2$—CO—CH$_2$—)$_s$; wherein m=1-5, q=5-15, r=3-7 and s=1-4; and wherein U is biotin, poly-histidine (6-10 residues), benzophenone, sulfhydryl, or aryl azide.

5. The compound of claim 4, wherein W and X are

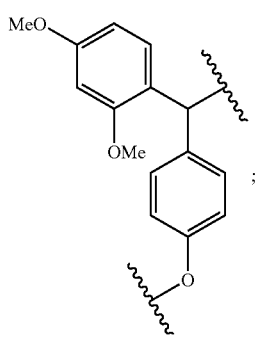

wherein Y is nothing; wherein Z is: (—CH$_2$—CH$_2$—O—)$_m$, where m=3; and
    wherein U is

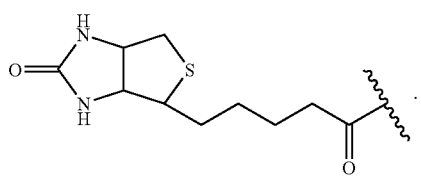

6. The compound of claim 4, wherein W and X are

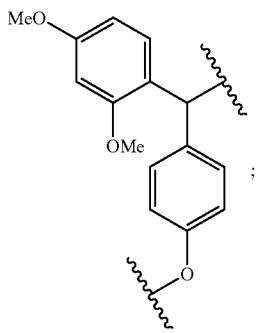

wherein Y is

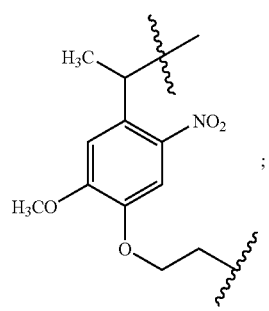

wherein Z is: (—CH$_2$—CH$_2$—O—)$_m$, where m=3; and
    wherein U is

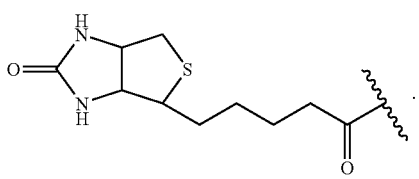

7. The compound of claim 4, wherein W and X are

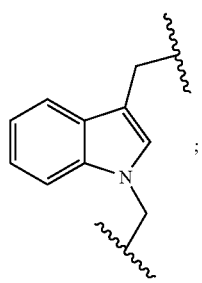

wherein Y is nothing; wherein Z is: (—CH$_2$—CH$_2$—O—)$_m$, where m=3; and wherein U is

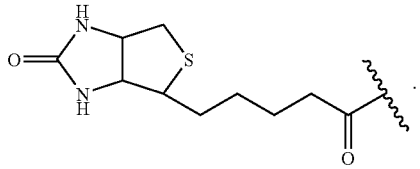

8. The compound of claim 4, wherein W and X are

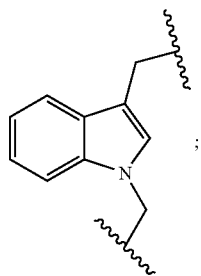

wherein Y is

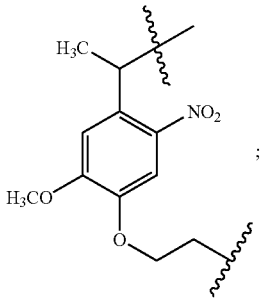

wherein Z is: (—CH$_2$—CH$_2$—O—)$_m$, where m=3; and
wherein U is

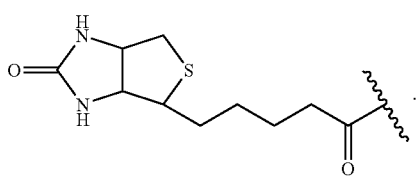

9. A composition, comprising a protein interaction reporter compound of Formula I of claim 1.

10. The composition of claim 9, wherein the compound is according to Formula I

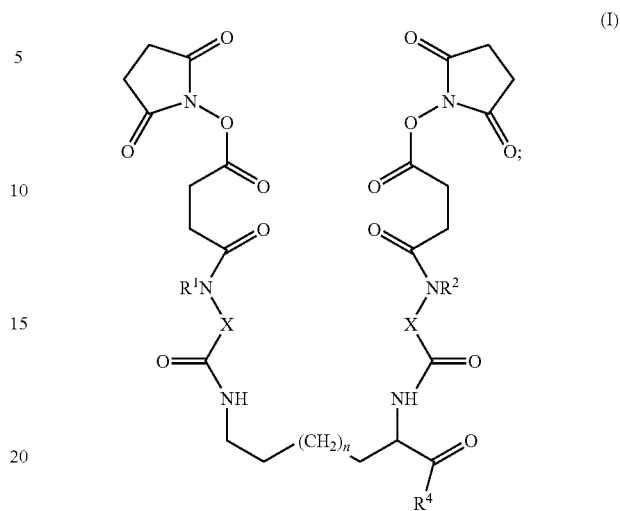

wherein: R$^1$ and R$^2$ are independently H, CH$_3$, or CH$_2$—CH$_3$;
n=1-6;
wherein R$^4$ is hydroxyl; and
wherein X is

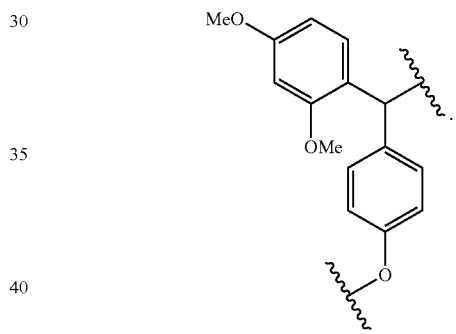

11. The composition of claim 9, wherein the compound is according to Formula I:

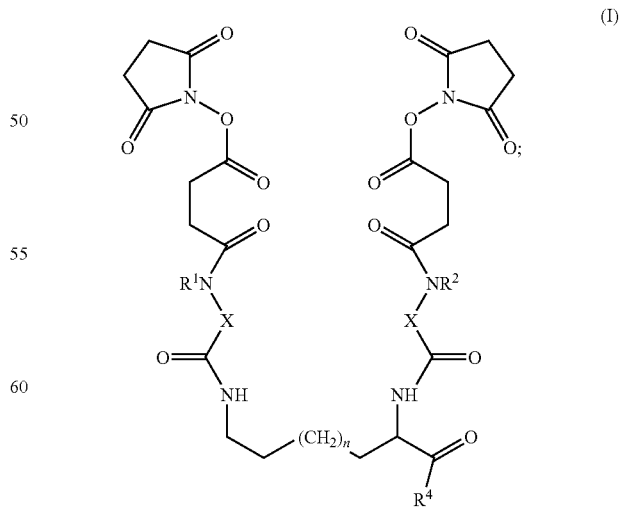

wherein: R$^1$ and R$^2$ are independently H, CH$_3$, or CH$_2$—CH$_3$;
n=1-6;

wherein R⁴ is

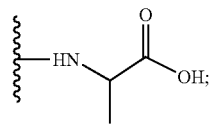

and
wherein X is

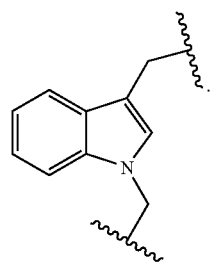

12. A composition, comprising a protein interaction reporter compound of Formula II of claim 4.

13. The composition of claim 12, wherein the compound is according to Formula II:

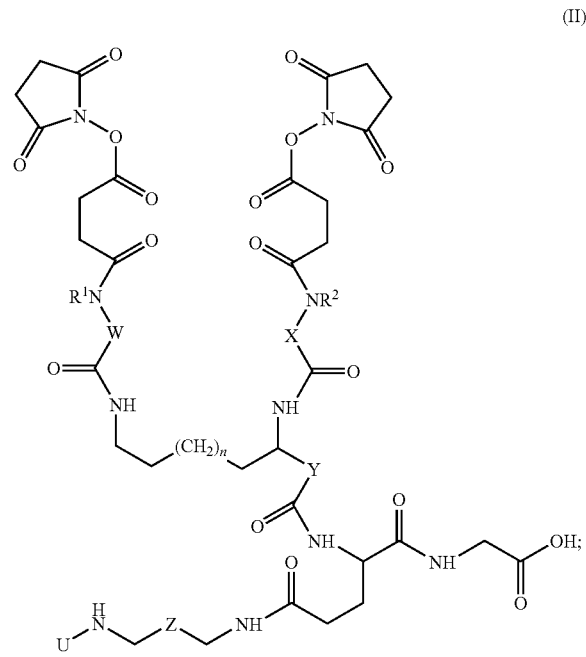

(II)

wherein R¹ and R² are independently selected from hydrogen, or $(C_1-C_4)$-alkyl;

wherein: n=1-6; and W and X are

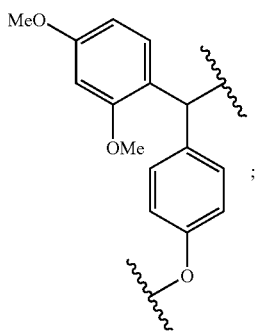

wherein Y is nothing; wherein Z is: $(-CH_2-CH_2-O-)_m$, where m=3; and
wherein U is

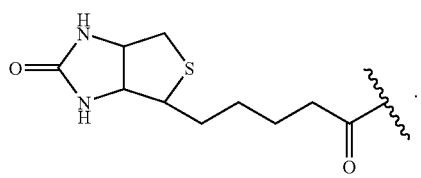

14. The composition of claim 12, wherein the compound is according to Formula II:

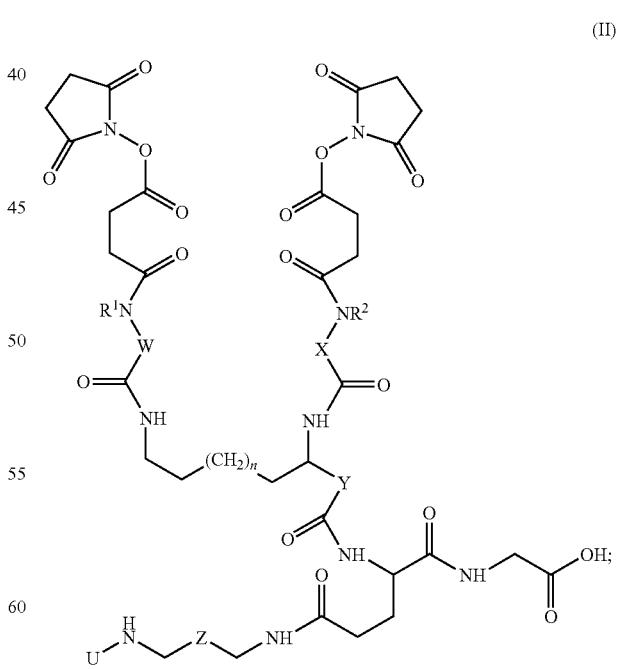

(II)

wherein R¹ and R² are independently selected from hydrogen, or $(C_1-C_4)$-alkyl;

wherein: n=1-6; and W and X are

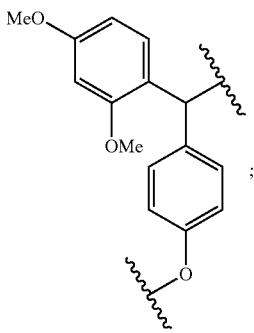

wherein Y is

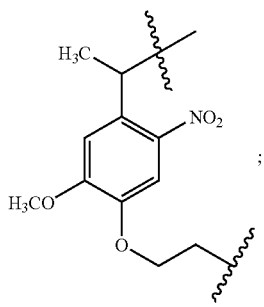

wherein Z is: (—CH$_2$—CH$_2$—O—)$_m$, where m=3; and wherein U is

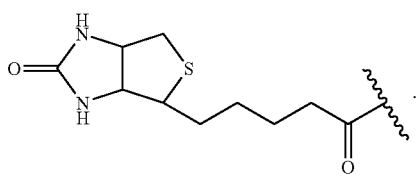

15. A method of identifying a protein participating in an intermolecular or intramolecular protein interaction, comprising:
   a) obtaining a sample comprising at least one protein;
   b) contacting the at least one protein with at least one multivalent protein interaction reporter (PIR) compound, under conditions suitable for cross-linking to provide a cross-linked protein sample product, wherein the PIR compound comprises at least two protein reactive moieties, each bound to a shared characteristic reporter moiety by a covalent labile bond, wherein the labile bonds, in each case, comprise a carbon-nitrogen bond that can be differentially cleaved with respect to peptide bonds, wherein the reporter moiety is operatively releasable from the PIR agent upon differential cleavage of the labile bonds to provide for a characteristic released reporter moiety;
   c) differentially cleaving the labile bonds of the cross-linked protein sample product to provide for cleavage products;
   d) subjecting the uncleaved and cleaved products to an analysis suitable to identify the cleavage products derived from the uncleaved products by virtue of being the reporter moiety or by inclusion of a protein reactive moiety or portion thereof;
   e) determining a peptide sequence associated with the protein reactive moiety or portion thereof; wherein protein participating in an intermolecular or intramolecular protein interaction is identified by comparing the peptide sequence to one or more known protein sequences, wherein the PIR is a compound of claim 1 or 4.

16. The method of claim 15, comprising, prior to c), digesting the cross-linked protein sample with at least one protease.

17. The method of claim 15, wherein the characteristic reporter moiety is a mass reporter moiety having a characteristic m/z value, the mass reporter moiety bound to each protein reactive moiety by a labile bond that is differentially cleavable with respect to peptide bonds by a method selected from the group consisting of collisional activation in a mass spectrometer, activation by electron capture dissociation (ECD), photoactivation and combinations thereof, and wherein subjecting the cleaved products to an analysis suitable to distinguish the cleavage products is, at least in part, by mass spectrometry.

18. The method of claim 17, wherein differential cleavage of the labile bonds is by applying a first ms activation energy sufficient to provide for a released mass reporter moiety having a characteristic m/z value, and to provide for a released polypeptide or peptide linked to a protein reactive moiety or portion thereof having a characteristic m/z value.

19. The method of claim 18, further comprising subjecting at least one cleaved product to a second, higher ms activation energy sufficient to fragment peptide bonds.

20. The method of claim 17, wherein the protein interaction reporter (PIR) compound is a compound according to Formula I:

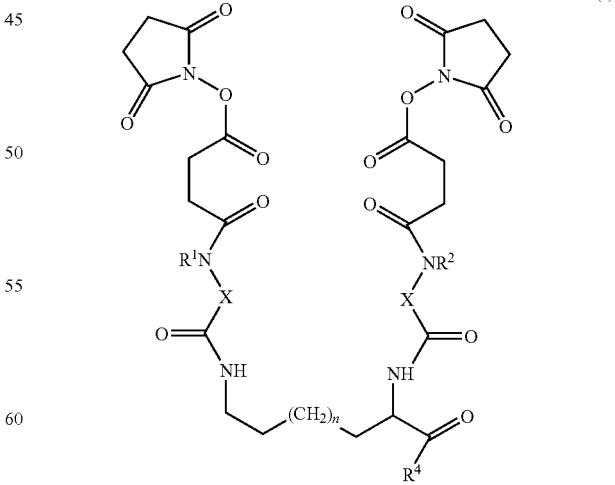

(I)

wherein: R$^1$ and R$^2$ are independently H, CH$^3$, or CH$_2$—CH$_3$; n=1-6;

wherein $R^4$ is hydroxyl, or

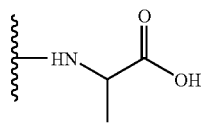

and wherein X is selected from the following:

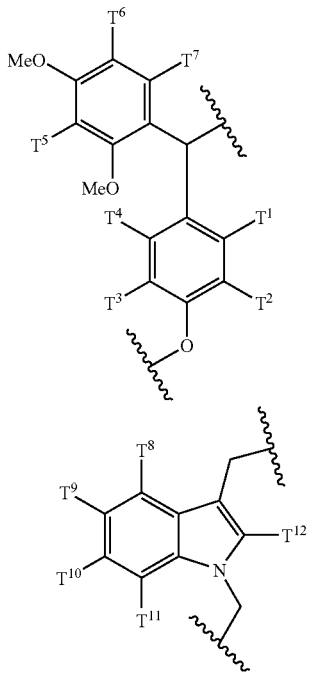

wherein $T^1$-$T^{12}$ are indegendently hydrogen, $(C_1$-$C_4)$-alkyl, or $(C_1$-$C_4)$-alkoxy.

21. The method of claim 17, wherein the protein interaction reporter (PIR) compound is a compound of Formula II:

(II)

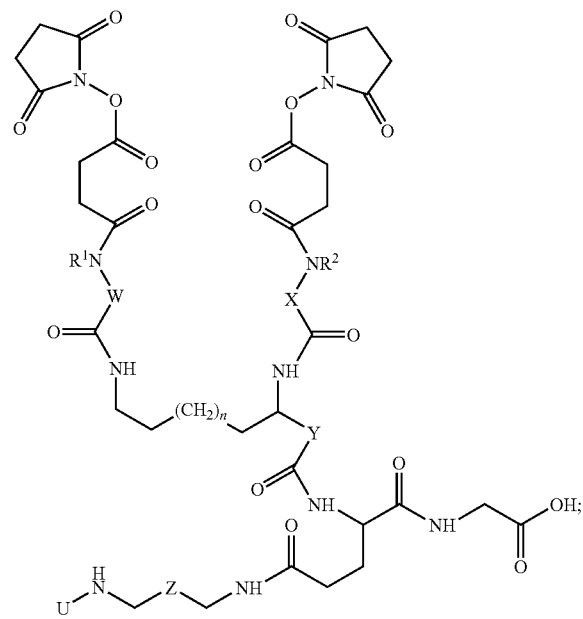

wherein $R^1$ and $R^2$ are independently selected from hydrogen, or $(C_1$-$C_4)$-alkyl;
wherein: n=1-6; and W and X are independently selected from:

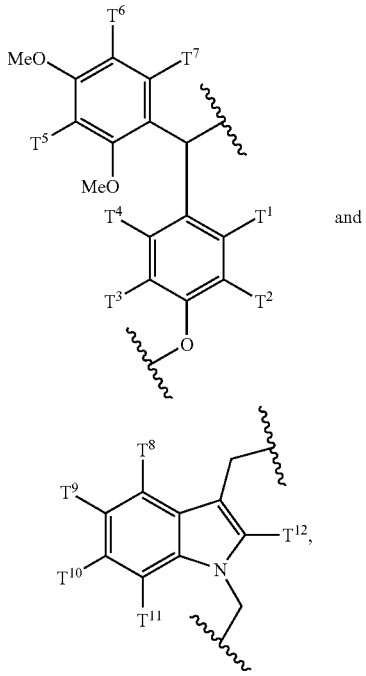

wherein $T^1$-$T^{12}$ are independently hydrogen, $(C_1$-$C_4)$-alkyl, or $(C_1$-$C_4)$-alkoxy;
wherein Y is nothing or wherein Z is: $(-CH_2-CH_2-O-)_m$; $(-CH_2-)_q$; $(-CO-CH_2-)_r$; $(-CH_2-CO_2-)_r$; $(-CH_2-CO-CH_2-CO_2-)_s$; wherein m=1-5, q=5-15, r=3-7 and s=1-4; and wherein U is biotin, poly-histidine (6-10 residues), benzophenone, sulfhydryl, or aryl azide.

22. The method of claim 15, wherein step b comprises contacting with a plurality of distinguishable protein interaction reporter (PIR) compounds.

23. The method of claim 20, wherein step b comprises contacting with a plurality of distinguishable protein interaction reporter (PIR) compounds of formula I of claim 1.

24. The method of claim 21, wherein step b comprises contacting with a plurality of distinguishable protein interaction reporter (PIR) compounds.

* * * * *